(12) United States Patent
Walls et al.

(10) Patent No.: US 8,834,934 B2
(45) Date of Patent: Sep. 16, 2014

(54) MATERIAL ENCAPSULATION SYSTEM

(75) Inventors: John E. Walls, Longmont, CO (US); Jeffrey W. Putt, Fort Collins, CO (US); Kenneth E. DeLine, Avon, CO (US)

(73) Assignee: Haviland Products Company, Grand Rapids, MI (US)

( * ) Notice: Subject to any disclaimer, the term of this patent is extended or adjusted under 35 U.S.C. 154(b) by 774 days.

(21) Appl. No.: 10/544,586

(22) PCT Filed: Feb. 11, 2004

(86) PCT No.: PCT/US2004/003834
§ 371 (c)(1), (2), (4) Date: Aug. 4, 2005

(87) PCT Pub. No.: WO2004/073033
PCT Pub. Date: Aug. 26, 2004

(65) Prior Publication Data
US 2006/0110464 A1    May 25, 2006

Related U.S. Application Data

(60) Provisional application No. 60/446,908, filed on Feb. 11, 2003.

(51) Int. Cl.
*A61K 9/16* (2006.01)

(52) U.S. Cl.
USPC .......................................................... 424/490

(58) Field of Classification Search
USPC .................... 424/490; 503/217; 510/130, 138
See application file for complete search history.

(56) References Cited

U.S. PATENT DOCUMENTS

| | | | | |
|---|---|---|---|---|
| 1,854,235 | A * | 4/1932 | Stoddard | 510/439 |
| 3,042,622 | A * | 7/1962 | Kirschenbauer | 510/100 |
| 3,250,680 | A | 5/1966 | Menkart et al. | |
| 3,329,616 | A * | 7/1967 | Feierstein et al. | 510/228 |
| 3,468,803 | A * | 9/1969 | Knapp et al. | 510/224 |
| 3,516,937 | A * | 6/1970 | Herrick et al. | 510/439 |
| 3,547,571 | A | 12/1970 | Angliker | |
| 3,627,693 | A | 12/1971 | Scarpelli | |
| 3,703,470 | A * | 11/1972 | Brennan | 510/231 |
| 3,839,220 | A | 10/1974 | Barchas | |
| 3,896,033 | A * | 7/1975 | Grimm, III | 510/519 |
| 3,926,830 | A * | 12/1975 | Horiguchi et al. | 510/100 |
| 4,362,715 | A | 12/1982 | Strianse et al. | |
| 4,379,143 | A | 4/1983 | Sherry et al. | |
| 4,626,550 | A | 12/1986 | Hertzenberg | |
| 4,668,422 | A * | 5/1987 | Malik et al. | 510/135 |
| 4,756,906 | A | 7/1988 | Sweeny | |
| 4,803,058 | A * | 2/1989 | Highfill | 510/534 |
| 4,839,081 | A | 6/1989 | Church et al. | |
| 4,861,627 | A | 8/1989 | Mathiowitz et al. | |
| 4,898,734 | A | 2/1990 | Mathiowitz et al. | |
| 4,917,893 | A * | 4/1990 | Okada et al. | 424/423 |
| 4,929,380 | A * | 5/1990 | Schulz et al. | 510/413 |
| 5,079,005 | A | 1/1992 | Gupta | |
| 5,104,646 | A | 4/1992 | Bolich, Jr. et al. | |
| 5,106,609 | A | 4/1992 | Bolich, Jr. et al. | |
| 5,238,915 | A | 8/1993 | Fuwa et al. | |
| 5,320,835 | A | 6/1994 | Pahlck et al. | |
| 5,384,364 | A * | 1/1995 | Besse et al. | 510/231 |
| 5,508,259 | A | 4/1996 | Holzner et al. | |
| 5,518,730 | A | 5/1996 | Fuisz | |
| 5,716,923 | A * | 2/1998 | MacBeath | 510/313 |
| 5,733,272 | A | 3/1998 | Brunner et al. | |
| 5,753,244 | A | 5/1998 | Reynolds et al. | |
| 5,771,925 | A | 6/1998 | Lewandowski | |
| 5,861,440 | A | 1/1999 | Gohla et al. | |
| 5,872,092 | A * | 2/1999 | Kong-Chan et al. | 510/413 |
| 5,912,017 | A | 6/1999 | Mathiowitz et al. | |
| 5,945,910 | A | 8/1999 | Gorra | |
| 5,985,354 | A | 11/1999 | Mathiowitz et al. | |
| 5,993,854 | A | 11/1999 | Needleman et al. | |
| 6,106,875 | A | 8/2000 | Soper et al. | |
| 6,107,261 | A | 8/2000 | Taylor | |
| 6,110,501 | A | 8/2000 | Redding, Jr. et al. | |
| 6,147,040 | A | 11/2000 | van der Hagen | |
| 6,270,783 | B1 | 8/2001 | Slavtcheff et al. | |
| 6,310,014 | B1 | 10/2001 | Rau | |
| 6,392,546 | B1 | 5/2002 | Smith | |

(Continued)

FOREIGN PATENT DOCUMENTS

DK   199 26 316    12/2000
EP   0382464       2/1990

(Continued)

OTHER PUBLICATIONS

Sigma Aldrich sigmaaldrich.com/chemistry/stockroom-reagents/learning-center/technical-library/particle-size-conversion.html, retrieved from the internet Jun. 25, 2009.*

(Continued)

*Primary Examiner* — Dennis Heyer
*Assistant Examiner* — Daniel M Podgorski
(74) *Attorney, Agent, or Firm* — Dickinson Wright PLLC

(57) ABSTRACT

A material encapsulation and release system having a first zone (1) containing a first amount of material (2) bound by a first capsule wall (3) and, if desired, a second zone (4) containing a second amount of material (5) bound by a second capsule wall (6), each capsule wall responsive to similar or dissimilar activation means (7) to release the first amount of material (2) in the first zone (1) and the second amount of material (5) in the second zone (4).

19 Claims, 5 Drawing Sheets

(56) References Cited

U.S. PATENT DOCUMENTS

Figure 1:
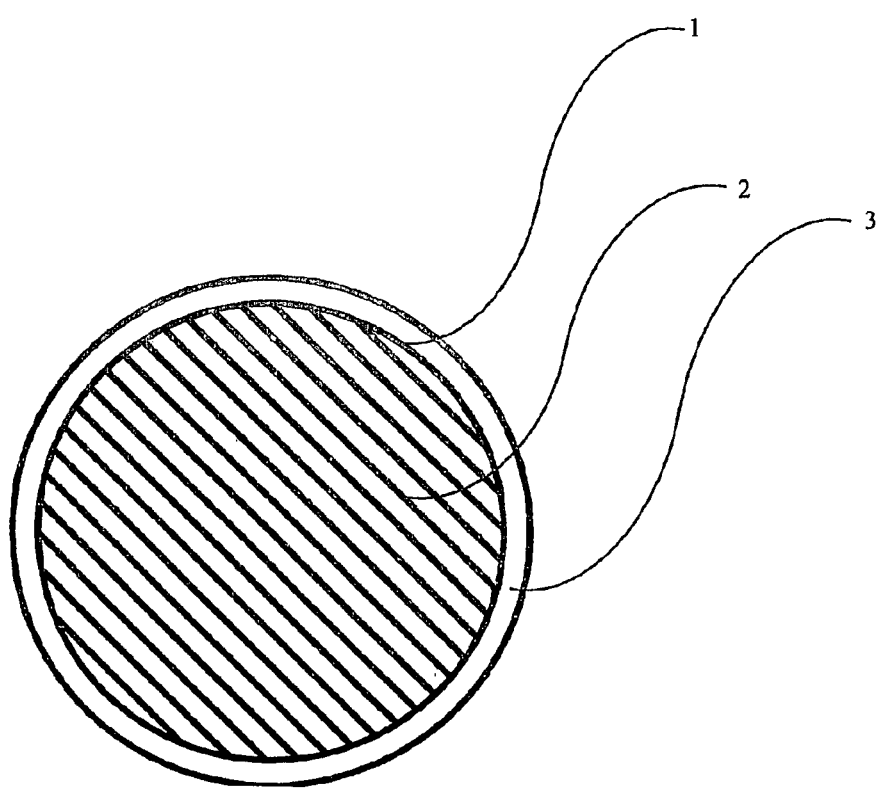

| | | |
|---|---|---|
| 6,432,421 B1 | 8/2002 | Brown et al. |
| 6,511,749 B1 | 1/2003 | Mathiowitz et al. |
| 2002/0022038 A1 | 2/2002 | Biatry et al. |
| 2002/0177534 A1 | 11/2002 | Paul |
| 2003/0060378 A1* | 3/2003 | Hsu et al. .................. 510/130 |
| 2003/0191036 A1* | 10/2003 | MacDonald et al. ......... 510/141 |
| 2006/0040835 A1 | 2/2006 | Newkirk et al. |

FOREIGN PATENT DOCUMENTS

| | | | | |
|---|---|---|---|---|
| EP | 1099764 | | 11/2000 | |
| FR | 2 717 184 | | 9/1995 | |
| FR | 2 805 162 | | 8/2001 | |
| GB | 1424714 A | * | 2/1976 | |
| WO | WO99/07817 | * | 2/1999 | ............... C11D 3/40 |
| WO | WO 99/40172 | | 8/1999 | |
| WO | WO 01/12148 | | 2/2001 | |
| WO | WO 01/12150 | | 2/2001 | |

OTHER PUBLICATIONS

Tyebkhan G. Indian J Dermatol Venereol Leprol 2001, 67, 290-1.*

Gelatin Properties in www.boith.com/food%20and%20feed%20product.files/Edible%20Gelatin.htm, retrieved from the internet Apr. 26, 2010.*

Indicator Table in Volumetric Analysis, Kolthoff and Stenge, Interscience Publisher's Inc., New York, 1942 and 1947.*

Decker et al. "A Rapid Method for the Presurgical Cleansing of Hands", Jan. 1978; 51(1), 115-117.

Harris, "A survey on handwashing practices and opinions of healthcare workers", Journal of Hospital Infection, 2000; 45; 318-321.

Larson et al., Effect of an Automated Sink on Handwashing Practices and Attitudes in High-Risk Units, Jul. 1991; 12(7) 422-427.

Larson, "APIC guideline for handwashing and hand antisepsis in health care settings", AJIC Am J Infect Control, Aug. 1995; 23(4), 251-269.

Naikoba et al., "The effectiveness of interventions aimed at increasing handwashing in heathcare workers—a systematic review", Journal of Hospital Infection, 2001; 43, 173-180.

Pittet et al., "Effectiveness of a hospital-wide programme to improve compliance with hand hygiene", The Lancet, Oct. 14, 2000; 356, 1307-1312.

Posfay-Barbe et al., "New Concepts in Hand Hygiene", Seminars in Pediatric Infectious Diseases, Apr. 2001; 12 (2), 147-153.

The Associated Press; "Hospital infections fourth leading cause of death", The Coloradoan, Jul. 21, 2002; p. A3.

* cited by examiner

MATERIAL ENCAPSULATION SYSTEM

This application is the United States National Stage of International Patent Cooperation Treaty Patent Application No. PCT/US04/03834, filed Feb. 11, 2004, and claims the benefit of U.S. Provisional Patent Application No. 60/446,908, filed Feb. 11, 2003, each hereby incorporated by reference herein.

I. TECHNICAL FIELD

A material encapsulation and release system having a first zone containing a first amount of material bound by a first capsule wall and, if desired, a second zone containing a second amount of material bound by a second capsule wall, each capsule wall responsive to similar or dissimilar activation means to release the first amount of material in the first zone and the second amount of material in the second zone.

II. BACKGROUND

Conventional microcapsules may provide a material within a capsule for use in controlled delivery systems. Conventional encapsulation technology may provide a capsule wall made of a first capsule layer adjoined directly with a second layer as described by U.S. Pat. Nos. 6,511,749; 5,985,354; 5,912,017; and 4,861,627, issued to Mathiowitz. Similarly, a single capsule may provide an intermixture of two polymeric layers as described by U.S. Pat. No. 3,627,693 issued to Scarpelli, hereby incorporated by reference herein.

While these conventional encapsulation technologies may in certain circumstances provide a single capsule wall having an interior capsule surface and an exterior capsule surface which exhibit different chemical properties allowing for encapsulation of a wider variety of materials, many problems with regard to the encapsulation and delivery of materials remain yet unresolved.

A significant problem with conventional encapsulation technology can be that the interior of a single capsule does not allow for the discrete separation of different amounts or kinds of material(s). As such, conventional capsules have an undivided interior volume which contains one kind of material.

Another significant problem with conventional encapsulation technology can be that the material contained within a single capsule cannot be released in discrete amounts in response to different discrete environmental circumstances. Conventional capsule walls rupture either because they degrade in response to exposure to a chemical environment or in response to the change in application of force on the capsule wall. Upon rupture the entire contents of the capsule are released. As such, while an amount of material may be released in response to a first discrete environmental circumstance, there is no mechanism by which conventional capsule technology can hold the release of a second discrete amount of material in abeyance until exposed to a second different discrete environmental circumstance.

Another problem with conventional encapsulation technology can be that separate capsules or mixtures of separate capsules may not deliver proportioned amounts of two different materials. Where different types of capsules each containing a different material are mixed, differential settling of the mixture or differential rupture of the two types of capsule mixes the contained materials in different proportions.

Another problem with conventional encapsulation technology can be failure to provide perceivable sensorial indicia of material release other than the perceivable sensorial indicia of the material itself, such as flavor, fragrance or color. In those instances of an encapsulated material having no sensorial indicia there may be no manner of ascertaining release of such material from a capsule.

Another problem with conventional encapsulation technology can be that release of encapsulated material does not further provide indicia coupled to discrete event occurrence. Material release from conventional capsule technology may provide pleasing sensorial attributes such as flavor, color, or fragrance. However, conventional encapsulation and delivery technology may not release flavor, color, or fragrance for the purpose of informing the user that a separate discrete event has occurred, such as therapeutic efficacy or the elapse of a predetermined length of time.

Another problem with conventional encapsulation technology can be the failure to further provide a carrier suitable for both conveyance of encapsulated material without rupture of the capsule walls and for washing hands. Specifically, as to conventional carriers suitable for washing hands, the carrier may not provide an encapsulated material released to indicate that a duration of hand washing has occurred, or achievement of efficacious hand washing with the carrier.

The instant invention addresses each of these concerns with respect to conventional encapsulation technology.

III. DISCLOSURE OF INVENTION

Accordingly, a broad object of the invention can be to provide a single capsule having a first zone containing a first material released in response to a first activation means which provides perceivable sensorial indicia of material release other than then the perceivable sensorial indicia inherent to the material itself, even if the released material itself does not provide perceivable sensorial indicia at all.

Another broad object of the invention can be to provide a single capsule having a first zone containing a first material released in response to a first activation means which provides perceivable sensorial indicia coupled to discrete event occurrence.

Another broad object of the invention can be to provide a single capsule having a first zone containing a first material released in response to a first activation means which acts upon a carrier to provide perceivable sensorial indicia of material release.

Another broad object of the invention can be to provide a single capsule having at least two zones which separate into discrete amounts at least two amounts of material.

Another significant object of the invention can be to provide a single capsule having a first zone which provides a first amount of material and at least one additional zone which provides a second amount of material released in response to an activation means.

Another significant object of the invention can be to provide a single capsule having a first zone containing a first amount of material released in response to first activation means and at least one additional zone containing a second amount of material released in response to second activation means, whether instant or disparate in time.

Another significant object of the invention can be to provide a capsule which can deliver in proportion a first amount of material and a second amount of material regardless of the number or rate at which capsules rupture.

Another significant object of the invention can be to deliver and release different materials from a single capsule obviating the need to mix different types of conventional capsules together.

Another significant object of the invention can be to release an amount of a first material and an amount of a second material in substantially contemporaneous, overlapped, or serial in time.

Another broad object of the invention can be to provide a single capsule having a first zone containing a first material released in response to a first activation means and a second zone containing a second material released in response to such first activation means or a second activation means which provides at least one perceivable sensorial indicia coupled to discrete event occurrence.

Naturally, further objects of the invention are disclosed throughout the specification and drawings.

IV. BRIEF DESCRIPTION OF THE DRAWINGS

FIG. 1 provides a cross section view of a particular embodiment of the invention which provides a capsule having first zone containing a first amount of material bound by a first capsule wall.

Figure 2:
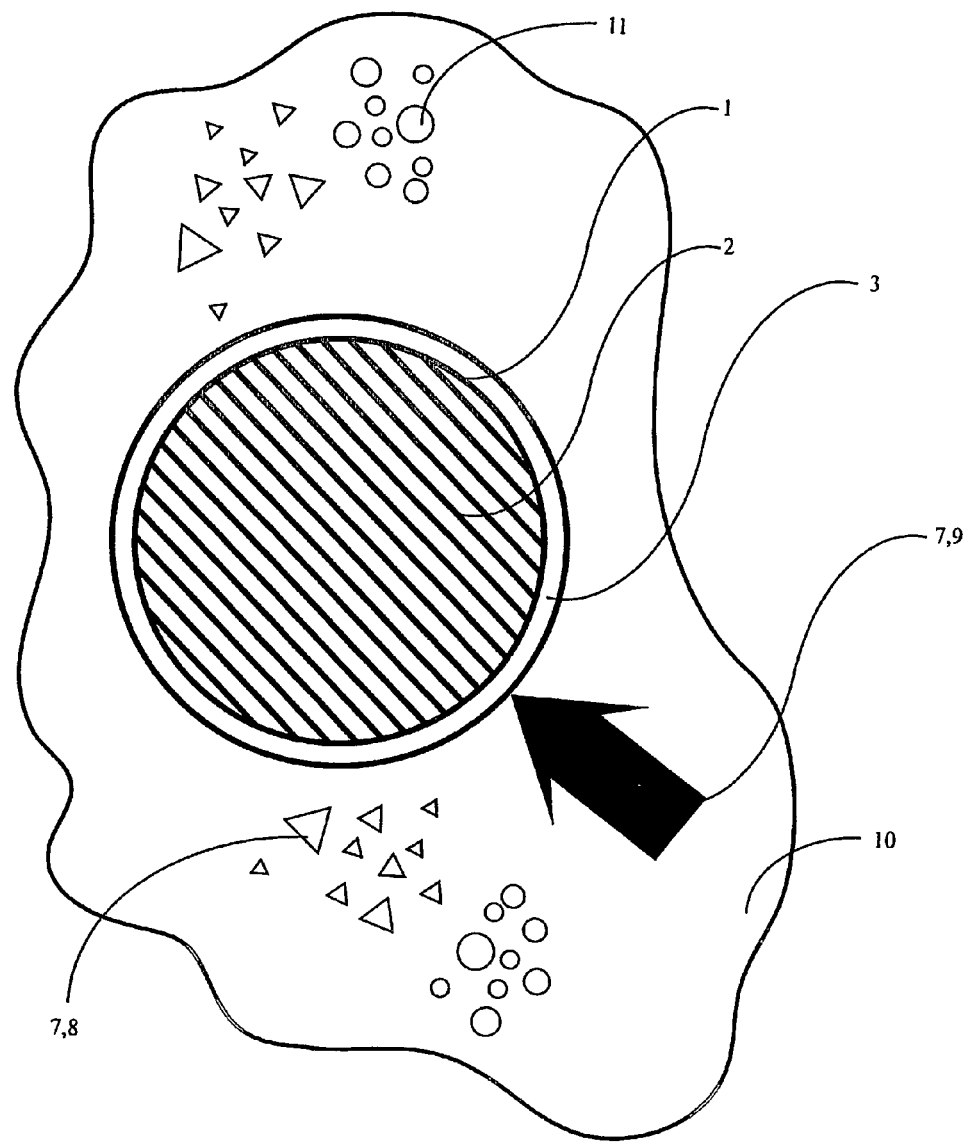

FIG. 2 provides a cross section view of a particular embodiment of the invention which provides a capsule having a first zone containing a first amount of material bound by a first capsule wall conveyed by a carrier.

Figure 3:
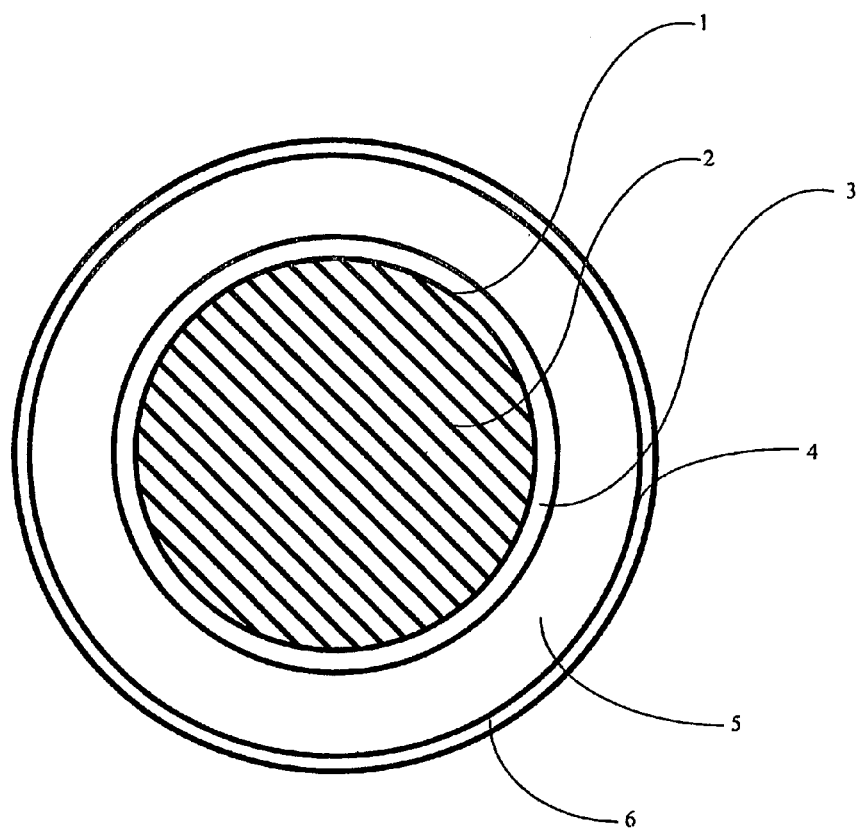

FIG. 3 provides a cross section view of a particular embodiment of the invention which provides a capsule having a first zone containing a first amount of material bound by a first capsule wall and a second zone containing a second amount of material bound by a second capsule wall.

Figure 4:
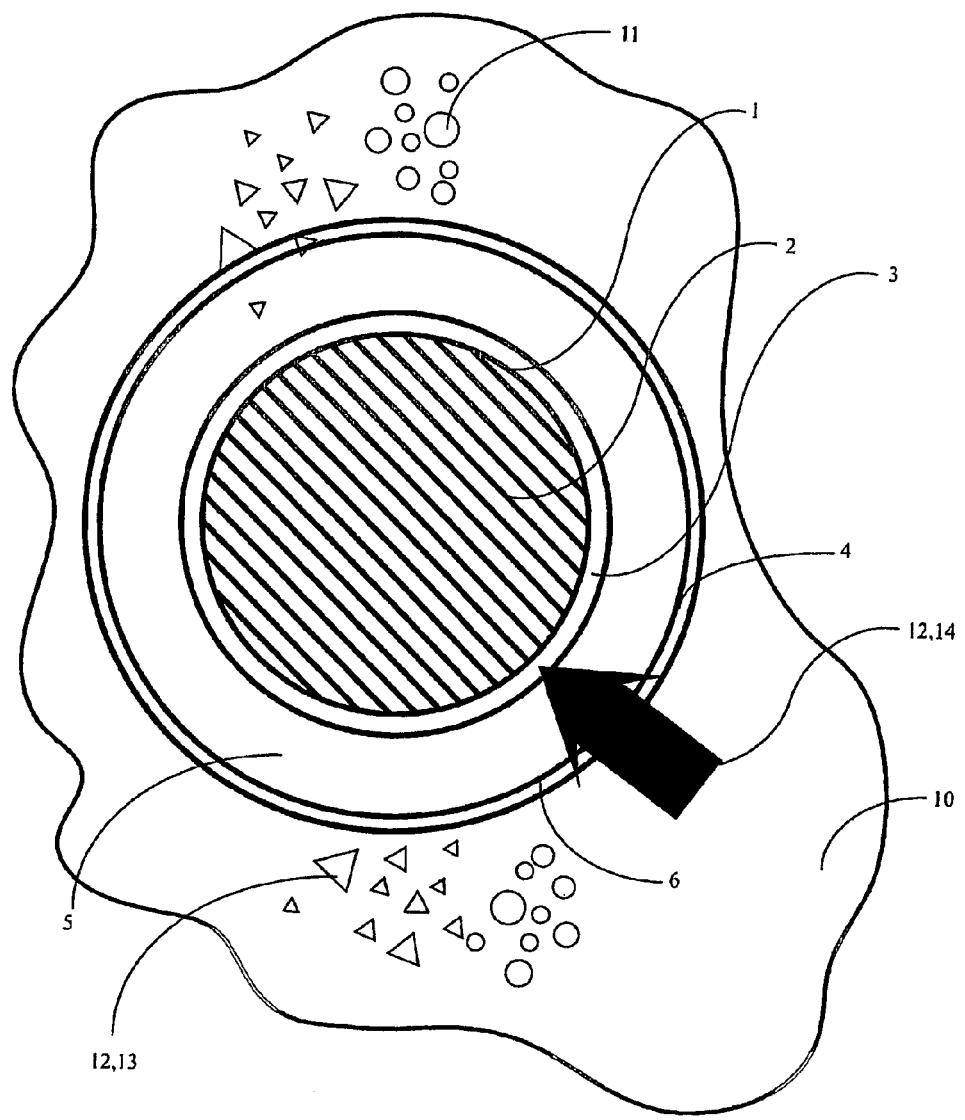

FIG. 4 provides a cross section view of a particular embodiment of the invention which provides a capsule having a first zone containing a first amount of material bound by a first capsule wall and a second zone containing a second amount of material bound by a second capsule wall conveyed in a carrier.

Figure 5:
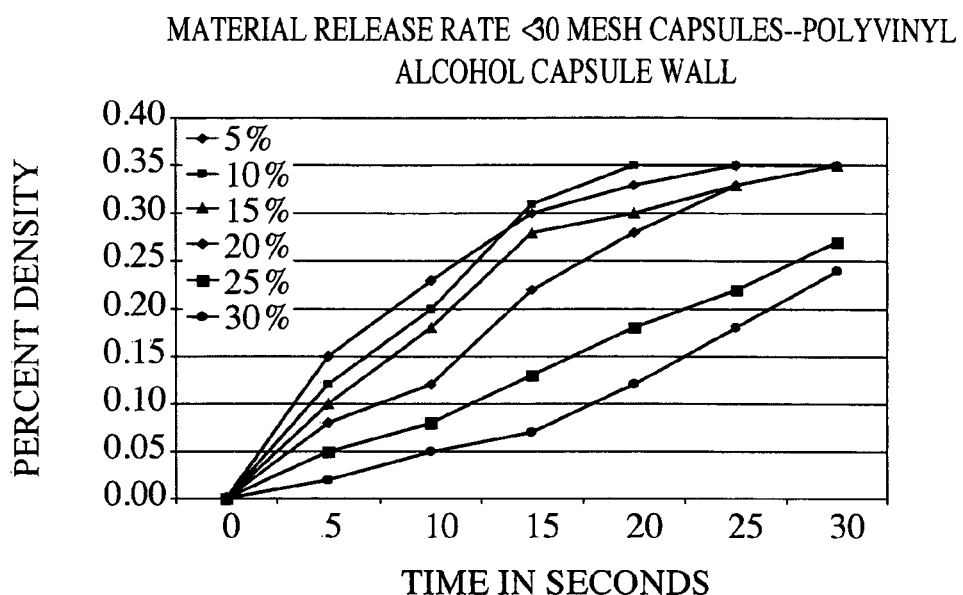

FIG. 5 plots percent density of water into which material has been released from capsules which have a capsule wall having a thickness represented as a percent increase over the size of the particle which the capsule wall coats versus time.

Figure 6:
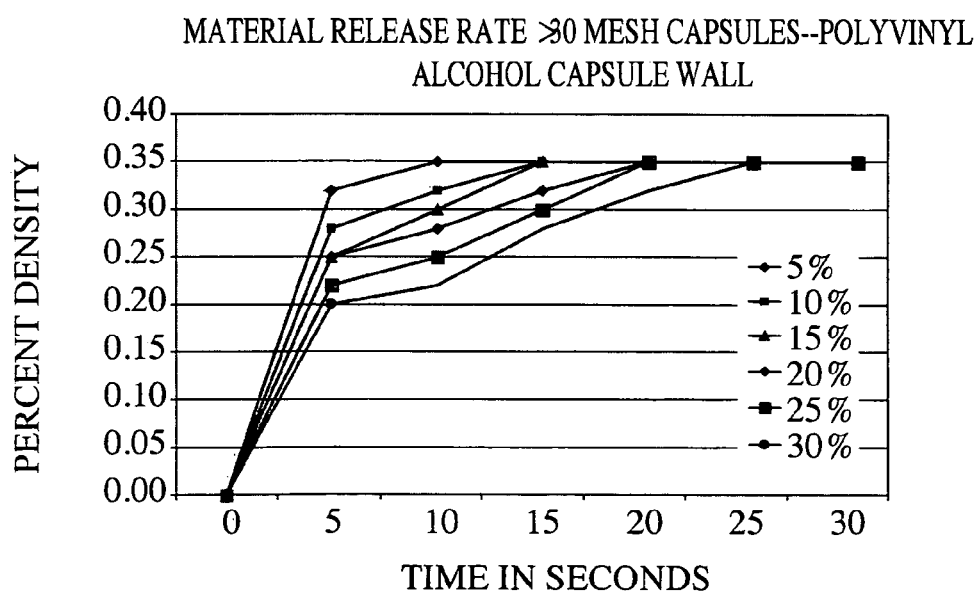

FIG. 6 plots percent density of water into which material has been released from capsules which have a capsule wall having a thickness represented as a percent increase over the size of the article which the capsule wall coats versus time.

V. MODE(S) FOR CARRYING OUT THE INVENTION

Generically, a material encapsulation and release system having a first zone (1) containing a first amount of material (2) bound by a first capsule wall (3) and, if desired, a second zone (4) containing a second amount of material (5) bound by a second capsule wall (6), each capsule wall responsive to similar or dissimilar activation means (7) to release the first amount of material (2) in the first zone (1) and the second amount of material (5) in the second zone (4).

Now referring primarily to FIG. 1, that shows a generic embodiment of the material encapsulation and release system having a first zone (1) containing a first amount of material (2) bound by a first capsule wall (3).

The first zone (1) defined by the inside surface of the first capsule wall (3) can be, but is not limited to, a substantially spherical, ovoid, or lozenge shaped volume. The configuration of the first capsule wall (3) to adjust volume of the first zone (1) to allow containment of the first amount of material (2), whether a solid or a liquid. As to certain embodiments of the invention, the first zone (1) can have a volume in the range of about one hundred nanoliters to about one microliter; however, the invention does not necessarily limit the first zone (1) to these relatively small volumes, and the first zone (1) can have a volume in excess of one microliter.

The first amount of material (2) contained within the first zone (1) can be any manner of useful material, substance, composition, mixture, colloidal suspension, or the like. The material can be either a liquid or a solid. The solids or liquids contained by the capsules may be aqueous soluble or non-aqueous soluble depending on the application, such as: surfactants, enzymes, flavors, fragrances, bleach or bleaching agents, pH change indicators, dyes, anti-statics, fabric softener, lubricants, emollients, insecticides, disinfectants, perfume, dentifrice, vaccines, drugs, medications, amino acids, nucleic acids, microbes, hormones, antiviral proteins, antiviral peptides, industrial chemicals (which includes a wide variety of materials such as oxidizing agents, reducing agents, free radical initiators, or the like), bioactive agents, lotions, gels, colloidal dispersions, or the like. These numerous solids or liquids may be further combined to impart or enhance moisturizing, lubricity, color, fragrance, texture, viscosity, or sound.

With respect to certain embodiments of the invention, the first amount of material (2) contained in the first zone (1) can be a base. The base can be one of the following non-limiting examples: sodium acetate, sodium carbonate, sodium bicarbonate, sodium borate, sodium citrate, sodium folate, sodium hydroxide, sodium phosphate dibasic, sodium phosphate tribasic, sodium polymetaphosphate, sodium pyrophosphate, sodium folate, sodium glycerophosphate, sodium ortho silicate, sodium meta silicate, sodium hypochlorite, sodium metaborate, sodium perborate, sodium tartrate, trisodium phosphate, potassium salts thereof, lithium salts thereof, individually or in various combinations.

Certain bases, such as trisodium phosphate, are available as anhydrous trisodium phosphate, and are available with various amounts of associated water such as five (5) moles, nine (9) moles, or twelve (12) moles of water, or the like, and any hydrated form of a base may be used as the first amount of material (2) in accordance with the invention.

With respect to other embodiments of the invention, the first amount of material (2) contained in the first zone (1) can be an acid. The acid can be one of the following non-limiting examples: methanoic acid, ethanoic acid, propanoic acid, butanoic acid, valeric acid, caproic acid, caprylic acid, capric acid, lauric acid, mylistic acid, palmitic acid, stearic acid, oleic acid, linoleic acid, linolenic acid, cyclohexanecarboxylic acid, phenylacetic acid, benzoic acid, oxalic acid, malonic acid, succinic acid, glutaric acid, adipic acid, pimelic acid, suberic acid, maleic acid, fumaric acid, phthalic acid, isophthalic acid, terephthalic acid, hemimellitic acid, trimellitic acid, trimesic acid, succinic anhydride, maleic anhydride, phthalic anhydride, glycolic acid, lactic acid, hydroxybutyric acid, mandelic acid, glyceric acid, malic acid, tartaric acid, citric acid, and ascorbic acid.

With respect to further embodiments of the invention, the first amount of material (1) contained in the first zone (1) can be a dye. The dye can be one of the following non-limiting examples: azo dye, disazo dye, diazonium salts, azoxy dye, hydrazo dye, benzidine dye, anthraquinone dye, triphenylmethane dye, aniline dye, aquonium dye, cationic dye, chrome dye, fluorescent dye, leuco dye, nitro dye, naphthol dye, toluidine dye, acridine dye, tetrakisazo dye, thiazole dye, fluorine dye, oxazin dye, tetraazolium salt dye, thiazin dye, pyronin dye, rhodamine dye, safranin dye, phthalocyanin dye, acid dye, base dye, and substituted analogs thereof.

The first amount of material (2) contained in the first zone (1) can comprise a particle. Whether the first amount of material (2) comprises a base particle, an acid particle, or a dye particle, a plurality of particles can be established between about 10 microns and 300 microns. By sieving the base particles, acid particles, or dye particles with different mesh (United States standard mesh, or otherwise) particle size between about 10 microns and about 30 microns, between about 20 microns and about 40 microns, between about 30 microns and about 50 microns, between about 40 microns and about 60 microns, between about 50 microns and about 70 microns, between about 60 microns and about 80 microns, between about 70 microns and about 90 microns, between about 80 microns and about 100 microns, between about 90 microns and about 110 microns, between about 100 microns and about 120 microns, between about 110 microns to about 130 microns, between about 120 microns to about 140 microns, between about 130 microns and about 150 microns, between about 140 microns to about 160 microns, between about 150 microns and about 170 microns, between about 160 microns to about 180 microns, between about 170 microns to about 190 microns, between about 180 microns to about 200 microns, between about 190 microns and about 210 microns, between about 200 microns and about 220 microns, between about 210 microns and about 230 microns, between about 220 microns and about 240 microns, between about 230 microns and about 250 microns, between about 240 microns to about 260 microns, between about 250 microns to about 270 microns, between about 260 microns and about 280 microns, between about 270 microns to about 290 microns, or between about 280 microns and about 300 microns, can be obtained.

As a non-limiting example, trisodium phosphate can be crushed and sieved to obtain a plurality of trisodium phosphate particles of between about 30 micron and about 250 micron. By selection of different sieves a plurality of trisodium phosphate particles of between about 40 micron and about 100 micron, or between about 50 micron and about 80 micron. A particular embodiment of the invention utilizes trisodium phosphate particles sieved through a first United States standard mesh 200 and then sieved through a second United States standard mesh 270.

Each particle of the base, acid, or dye as described above can comprise as to some embodiments of the invention, the first amount of material (2) contained in the first zone (1). As to these embodiments of the invention in which the first amount of material (2) comprises a particle, the particle can be bounded by a capsule wall (3) or coat applied by fluid bed process (also known as Würster Process). Particles to be coated are placed in a chamber where air is injected from below, whereby particles are suspend in the circulating air. Depending on the composition of the capsule wall or coat material it is dissolved in either water or a solvent. The capsule wall or coat material can then be sprayed into the chamber where it is adsorbed onto the surface of the particles. Warm air can facilitate removal of excess water or solvent from the capsule wall or coat material applied to the particle.

A wide variety of capsule wall or coat materials can be applied by fluid bed process including, individually or as mixtures: polyvinyl alcohol, polyvinyl alcohol/ethylene copolymer, polyvinyl pyrolidone, polyvinyl pyrrolidone/acetate copolymer, polyvinyl methyl ether, polyvinyl methyl ether/maleic anhydride copolymer, polyvinyl methyl ether/maleic acid half ester copolymer, polyacrylamide, poly(acrylamide/acrylic acid) copolymer, polyacrylic acid, polyallylamine, poly(4-ammonium styrenesulfonic acid), poly (diallyldimethylammonium chloride), poly(ethylene/acrylic acid) copolymer, poly(ethylene/1,2-butylene)diol, polyethylene glycol mw>6000, poly(ethylene glycol) methyl ether, poly(ethylene glycol)dimethyl ether, poly(ethylene glycol/propylene glycol)monobutyl ether, poly(2-ethyl-2-oxazoline), poly(hexamethylene adipate)diol, poly(hexamethylene carbonate)diol, poly(neopentyl adipate), poly(neopentyl sebacate), poly(polytetrahydrofuran carbonate)diol, poly(sodium 4-styrene sulfonate), poly styrene sulfonic acid, polyvinyl phosphonic acid, poly(4-vinylpyridine), tapioca dextrin, maize dextrin, waxy dextrin, starch, methyl cellulose, ethyl cellulos, hydroxy ethyl cellulose, isopropyl cellulose, hydroxy isopropyl cellulose, agar-agar, carrageenan, carboxymethylcellulose, polyasparatate, acacia, and gum tragacanth.

The fluid bed process can continue until the desired level of coating is achieved. Typically, the level of coating is described as percent increase of the original particle size. As a non-limiting example, the trisodium phosphate particles described above of between about 50 micron and 80 micron can be coated with fully hydrolyzed polyvinyl alcohol (molecular weight of about 4000)(commercially available under the brand name Celvol 107) to increase the size of the trisodium phosphate particle between about five percent and about thirty percent. The fluid bed process can be adjusted to obtain a percent increase in particle size using fully hydrolyzed polyvinyl alcohol or other capsule wall or coat material of between about 3% and about 5%, about 5%, between about 5% and about 7%, between about 7% and about 9%, about 10%, between about 9% and about 11%, between 11% and about 13%, between about 13% and about 15%, about 15%, between 15% and about 17%, between about 17% and about 19%, between about 19% and about 21%, about 20%, about 21% and about 23%, about 23% and about 25%, about 25%, about 25% and about 27%, about 27% to 29%, about 29% to about 31%, or about 30%.

With respect to a wide variety of embodiments of the invention prepared utilizing the fluid bed process, the first capsule wall (3) can have a thickness selected between about 2 microns and about 45 microns. Narrow ranges in capsule wall thickness can be achieved with the above-described capsule wall or coat materials such that the first capsule wall (3) or coat can have a thickness selected from between about 2 microns to about 6 microns, between about 4 microns to about 8 microns, between about 6 microns to about 10 microns, between about 8 microns and about 12 microns, between about 10 microns and about 14 microns, between about 12 microns and about 16 microns, between about 14 microns and about 18 microns, between about 16 microns and about 20 microns, between about 18 microns to about 22 microns, between about 20 microns to about 24 microns, between about 22 microns to about 26 microns, between about 24 microns and about 28 microns, between about 26 microns and about 30 microns, between about 28 microns and about 32 microns, between about 30 microns and about 34 microns, between about 32 microns and about 36 microns, between about 34 microns and about 38 microns, between about 36 microns and about 40 microns, between about 38 microns and about 42 microns, between about 40 microns and about 44 microns, and about 42 microns and about 46 microns.

The resulting capsule can have a size between about 10 microns and about 300 microns from which narrow ranges of capsule size can be used for particular applications. Capsules can be obtained within narrow size ranges including without limitation between about 15 microns to about 30 microns, between about 20 microns to about 40 microns, between about 30 microns to about 50 microns, between about 40 microns to about 60 microns, between about 500 microns to about 70 microns, between about 60 microns to about 80 microns, between about 70 microns to about 90 microns, between about 80 microns to about 100 microns, between about 90 microns to about 110 microns, between about 100 microns to about 120 microns, between about 110 microns to about 130 microns, between about 120 microns to about 140 microns, between about 130 microns to about 150 microns, between about 140 microns to about 160 microns, between about 150 microns to about 170 microns, between about 160 microns to about 180 microns, between about 170 microns to about 190 microns, between about 180 microns to about 200 microns, between about 190 microns to about 210 microns, and so forth up to about 300 microns.

Adjustment of the capsule size and the thickness of the capsule wall can yield a controllable spectrum of material release rates from the capsules. Now referring to FIGS. 5 and 6, with respect to a capsule wall (3) comprised of polyvinyl alcohol, the larger the capsule the more rapid the release of material from the capsule when exposed to an activation element (7) comprising water (even though the capsule wall remains the same thickness). Also, the thinner the capsule wall (3) the more rapid the release of material from the capsule when exposed to an activation (7) comprising water.

Now referring to FIGS. 1 and 2 which plot Percent Density of water into which material has been released (greater amount of released material the greater the density) from capsules have a capsule wall having a thickness represented as a percent increase over the size of the particle which the capsule wall coats (5%, 10%, 15%, 20%, 25%, 30%) versus time.

Again referring primarily to FIG. 1, the first amount of material (2) can comprise an amount of liquid, such as a solution of base, a solution of acid, or a solution of dye, or an oil such as: lemon oil, lime oil, vanilla oil, wintergreen oil, spearamint oil, sandalwood oil, musk oil, jojoba oil, bergamot oil, casis oil, lavender oil, chamomile oil, valerian oil, peony oil, rose oil, St. John's wort oil, cypress oil, rosemary oil, ylang ylang oil, passionflower oil, neroli oil, cedarwood oil, Frankincense oil, lemongrass oil, orange oil, mandarin oil, witch hazel, cucumber oil, aloe oil, juniper oil, sage oil, pomegranate oil, mint oil, gardenia oil, jasmine oil, narcissus oil, lilac oil, magnolia oil, honeysuckle oil, apricot oil, blackberry oil, papaya oil, huckleberry oil, kiwi oil, mango oil, bayberry oil, clove oil, eucalyptus oil, amaretto oil, cinnamon oil, and sesame oil.

Particles and liquids not miscible in water, or materials soluble in liquids not miscible in water, may be encapsulated using coacervation process. The two immiscible liquids are mixed together under high speed shear mixing. As the shear is increased, the liquid not water miscible is broken into tiny droplets. A water soluble capsule wall material, such as gelatin, can be provided in the aqueous portion of the mixture. When the droplets are of the desired size, the water soluble capsule material can be salted out of solution by the addition of materials that reduce the solubility of the capsule material. A variety of materials that are water soluble can be added to the mixture which reduces the solubility of the gelatin. As the capsule wall material is pushed out of solution, it is adsorbed onto the droplets. When gelatin is used it may re-dissolve if the equilibrium is disturbed. Therefore, as to those embodiments utilizing gelatin as a capsule wall material a cross-linking agent can be used to harden the gelatin, such as an aldehyde. A most useful aldehyde is glutaraldehyde. The aldehyde will harden the gelatin so that when mixing is complete, it may be filtered, washed and remain in tact.

Used to a lesser degree is a coacervation method where a capsule wall material soluble in solvent may be used by saturating the solvent and force the coating substance out of solution to be adsorbed onto a particle or droplet. Typically another solvent that is miscible with the first solvent, but is not a solvent for the substance being coated is preferred.

Now referring primarily to FIG. 2, the capsules described above can be mixed into a carrier (10). The carrier can be selected to avoid or limit degradation of the first capsule wall (3) to prevent the first amount of material (2) from release into the carrier (10). As such, a capsule wall material can be selected which avoids release of the first amount of material into one or more carriers, without limitation ethylene glycol, propylene glycol, polyethylene glycol, polypropylene glycol, poly(ethylene glycol/propylene glycol), 1,3-propanediol, 1,2-butanediol, 2,3-butanediol, 1,4-butanediol, 1,6-hexanediol, pinacol, glycerol, neopentylglycol, pentaerythritol, meso-hydrobenzoin, 1,2-cyclopentanediol, 1,2-cyclohexanediol, methanol, ethanol, isopropanol, n-propanol, n-butanol, isobutanol, sec-butanol, tert-butanol, n-pentanol, isopentanol, amyl alcohol, tert-pentanol, cyclopentanol, cyclohexanol, n-hexanol, n-heptanol, n-octanol, n-nonanol. n-decanol, n-dodecanol n-tetradecanol, n-hexadecanol, n-octadecanol, phenoxyethanol, benzyl alcohol, diphenyl carbinol, tetraphenylcarbinol, methoxyethanol, ethoxyethanol, propoxyethanol, butoxyethanol, hexoxyethanol, methoxypropanol, ethoxypropanol, propoxypropanol, butoxyepropanol, hexoxypropanol, ethoxyethoxy methanol, ethoxyethoxy ethanol, ethoxyethoxy propanol, ethoxyethoxy butanol, ethoxyethoxy hexanol, propoxypropoxy methanol, propoxypropoxy ethanol, propoxypropoxy propanol, propoxypropoxy butanol, propoxypropoxy hexanol.

The carrier (10) can further include an amount of indicator material (11). The indicator material can be a color change material which as a non-limiting example can be responsive to altered pH or final pH of the carrier (10). As to some embodiments of the invention the indicator material may have a first color in a first pH range of about 5.0 pH and about 7.0 pH, such as brilliant yellow, bromthylmol blue, m-nitrophenol, neutral red, phenophtalein. The indicator material may have a second color in a second pH range of about 7.0 and about 9.4. As such, the indicator material (11) can provide the carrier (10) with a first color in the first pH range and a second color in the second pH range.

Other embodiments of the invention can utilize indicator materials that have a first pH range and a second pH range above about 7.0 pH. As to these embodiments a first color and a second color can be obtained for the same carrier (10) at alkaline pH utilizing as a non-limiting examples: alizarin red S, alkali blue, clayton yellow, cresol red, curcumin, m-cresol purple, o-cresophthalein, phenol violet, p-naphtholbenzein, thymol violet, thymolphtalein, or titan yellow.

Similarly other embodiments of the invention can utilize indicator materials that have a first pH range and a second pH range at about or below 7.0 pH. As to these embodiments a first color and a second color can be obtained for the same carrier (10) at acid pH utilizing as a non-limiting examples: alzarin red, bromcresol green, bromcresol purple, bromcresol blue, congo red, crystal violet, dimethyl yellow, ethyl violet, malachite green, m-cresol purple, ntanil yellow, methyl orange, methyl purple, methyl red, methyl violet, phenol red, resorcin blue, and thymol blue.

Numerous and varied compositions can be achieved by varying the first amount of material (2), the first capsule wall or coat (3), the carrier (10) and the indicator material (11). The following non-limiting examples provide wash agents with a color changing carrier include:

A first amount of material (2) comprising an amount of citric acid, and wherein the capsule wall (3) or coat comprises polyvinyl alcohol, and wherein the carrier (10) comprises a mixture of:

a. an amount of polypropelene glycol (2000);
b. an amount of Miracare MP35;
c. an amount of Tegosoft PSE 141G; and
d. an amount of sodium phosphate monobasic;
and wherein the amount of indicator material (11) comprises an amount of methyl orange in the carrier (10).

A first amount of material (2) comprising trisodium phosphate, and wherein the capsule wall (3) or coat comprises polyvinyl alcohol, and wherein the carrier (10) comprises a mixture of:
a. an amount of polypropelene glycol (2000);
b. an amount of Miracare MP35; and
c. an amount of Tegosoft PSE 141G;
and wherein the amount of indicator material (11) comprises an amount of phenolphthalein in the carrier (10).

A first amount of material (2) comprising trisodium phosphate, and wherein the capsule wall (3) or coat comprises polyvinyl alcohol, and wherein said carrier (10) comprises a mixture of:
a. an amount of polypropelene glycol (2000);
b. an amount of Miracare MP35;
c. an amount of Tegosoft PSE 141G; and
d. an amount of sodium bicarbonate;
and wherein the amount of indicator material (11) comprises an amount of methyl orange.

A first amount of material (2) comprising trisodium phosphate, and wherein the capsule wall (3) or coat comprises polyvinyl alcohol, and wherein the carrier (10) comprises a mixture of:
a. an amount of polypropelene glycol (2000);
b. an amount of Miracare MP35;
c. an amount of Tegosoft PSE 141G; and
d. an amount of sodium bicarbonate;
and wherein the amount of indicator material (11) comprises an amount of phenol violet.

A first amount of material (2) comprises citric acid, and wherein the capsule wall (3) or coat comprises said polyvinyl acetate-paraffin wax, and wherein the carrier (10) comprises a mixture of:
a. an amount of water;
b. an amount of ammonium lauryl sulfate;
c. an amount of Silwet L-7220;
d. an amount of Tegosoft PSE 141G; and
e. an amount of sodium phosphate monobasic;
and wherein the amount of indicator material (11) comprises an amount of said methyl orange.

A first amount of material (2) comprises said amount of sodium triphosphate, and wherein the capsule wall (3) or coat comprises said polyvinyl acetate-paraffin wax, and wherein the carrier (10) comprises a mixture of:
a. an amount of water;
b. an amount of ammonium lauryl sulfate;
c. an amount of Silwet L-7220;
d. an amount of Tegosoft PSE 141G; and
e. an amount of sodium phosphate monobasic;
and wherein the amount of indicator material (11) comprises and amount of said phenolphtalein.

The following non-limiting examples provide wash agents with a indicator material (11) comprising either copious amounts of foam generated by the carrier or sound generated by rupture of the bubbles comprising the foam:

A first amount of material (2) comprising citric acid, and wherein the capsule wall (3) or coat comprises polyvinyl acetate-paraffin wax, and wherein said carrier comprises a mixture of:
a. an amount of polypropelene glycol (2000);
b. an amount of Miracare MP35;
c. an amount of Tegosoft PSE 141G; and
d. an amount of sodium bicarbonate.

A first amount of material (2) comprising citric acid, and wherein the capsule wall (3) or coat comprises polyvinyl alcohol (Cevol 107), and wherein the carrier (10) comprises a mixture of:
a. an amount of polypropelene glycol (2000);
b. an amount of Miracare MP35;
c. an amount of Tegosoft PSE 141G; and
d. an amount of sodium bicarbonate.

Now again referring to FIG. 2, each of the preceding non-limiting examples provides a first capsule wall (3) which remains substantially dormant in the carrier (10) until presented to a first activation element (7). The first activation element (7) acts upon the first capsule wall (3) to release the first amount of material (2) contained in the first zone (1).

With respect to certain capsule wall or coat materials, the first activation element (7) can comprise an activation material (8) which without limitation can be an alcohol, an ether, a glycol ether, a dihydric alcohol, a polyol, a lactone, or water. With respect to various embodiments of the invention, the first activation element corresponds to the chemical environment at a particular step in a process. As a non-limiting example, the application of an amount of water during hand washing.

With respect to other embodiments of the invention, the capsule wall or coat materials can be made responsive to a first activation element (7) comprising an amount of force (9) caused by change in motion, change in pressure, or the like. As a non-limiting example, the capsule wall material can be selected and configured to be responsive to the forces generated during efficacious hand washing.

With respect to the embodiments of the invention above-described having a capsule wall (3) of polyvinyl alcohol the first activation element (7)(8) comprises an amount of water. When presented with water the capsule wall (3) degrades and ruptures releasing the first amount of material (2) into the carrier (10). As to those carriers having an indicator material (11) comprising a color change material responsive to change of pH, if the capsule releases base or acid the carrier (10) can change color. As to those carriers having an amount of base, release of acid from the capsule can generate copious amounts of foam or sound.

With respect to the embodiments of the invention above-described having a capsule wall (3) of polyvinyl acetate-paraffin wax the first activation element (7)(9) comprises an amount of force. When presented with sufficient force from within or from without the capsule wall (3) degrades or ruptures to release said first amount of material (2). Again, as to those carriers having an indicator material (11) comprising a color change material responsive to change of pH, if the capsule releases base or acid the carrier (10) can change color. As to those carriers having an amount of base, release of acid from the capsule can generate copious amounts of foam or sound.

Understandably, the composition or thickness, or both the composition and thickness, of the capsule can be adjusted as above-described to delay release of the first amount of material (2) from the time presented with the first activation element (7). As such, perceivable sensorial indicia (color, color change, fragrance, sound, foam generation, and the like) can occur substantially coincident with or be coupled to discrete event occurrence.

Now referring primarily to FIG. 3, the invention can further include a second zone (4) containing a second amount of material (5) bound by a second capsule wall (6) or coat. The second zone (4) can also have various boundary configurations which may include, but are not limited to, substantially spherical, ovoid, lozenge, or the like which define the volume of the second zone (4).

The second amount of material (5) contained in the second zone (4) can be the same as the first amount of material (2) or a different material, including, but not limited to, any of the above-described materials use as the first amount of material (2), such as a base, an acid, a dye, an indicator material, a color change material, or pH color change material. The second amount of material (5) can engage a portion or all of the exterior surface of the first capsule wall (3). As such, the second amount of material must not degrade, solubilize, or act upon the first capsule wall (3) to release the first amount of material (2). Embodiments of the invention provide solutions to this problem in at least three ways. First, the first amount of material (2) contained in the first zone (1), the first capsule wall (2), and the second amount of material (5) in the second zone (4) can be chemically coordinated such that the first capsule wall (3) is selected to resist degradation by the first amount of material (2) contained in the first zone (1) and the second amount of material (5) contained in the second zone (4). Second, the first amount of material (2) and the second amount of material (5) can both be selected to avoid degradation of the first capsule wall (3). Third, the first capsule wall (3) can comprise two layers—an inside layer of the first capsule wall (3) to resistant degradation by the first amount of material (2) contained in the first zone (1) and an outside layer of the first capsule wall (3) to resistant degradation by the second amount of material (5) contained in the second zone (4).

The second amount of material can be deposited on the exterior surface of the first capsule wall (3) by fluid bed process, vapor phase process (the material to be applied is vaporized under low vacuum and high temperature and injected toward the first capsule wall (3) to be coated), prilling (spraying the capsules into a solution of the second amount of material), evaporative coating (dipping the capsules in a solution of the second amount of material and drying).

The invention can further include a second capsule wall (6) configured to the boundary of the second zone (4). The second capsule wall (6) can be selected from the capsule wall materials as above-described. As such, the second capsule wall can be selected to resist degradation by the second amount of material (5) contained by the second zone (4) and by the carrier (11) into which the multiple zone capsules are mixed. Again, as for the first capsule wall, embodiments of the invention may utilize two layers to present capsule wall material which resist the second amount of material (5) and the carrier (10) which may be one or a combination of the carrier materials above-described.

Again, the multiple zone capsule provides a second capsule wall (3) which remains substantially dormant in the carrier (11) until presented to a second activation element ( ). The second activation element (7) acts upon the second capsule wall (3) to release the second amount of material (2) contained in the second zone (1).

With respect to certain second capsule wall or coat materials, the second activation element (12) can comprise an activation material (13) which without limitation can be an alcohol, an ether, a glycol ether, a dihydric alcohol, a polyol, a lactone, or water.

The second activation element (12) can alternately comprise an amount of force (14) caused by change in motion, change in pressure, or the lice. As a non-limiting example, the capsule wall material can be selected and configured to be responsive to the forces generated during efficacious hand washing.

The second activation element (12) can be coupled to a single step in a process into which both the second amount of material and the first amount of material are released substantially coincidentally, staggered, serially, or serially separated by an elapse of time. The release of the second amount of material (5) or the release of the first amount of material (2) can provide perceivable sensorial indicia which can be coupled to the occurrence of a discrete event or provide a reinforcer to induce the user to continue use of the composition until the discrete event, or used in various combinations or permutations of both.

The first activation element (7) and the second activation element (12) can alternately be coupled to two discrete steps, or where the second activation element mixed with the second amount of material creates the first activation element for release of the first amount of material (2).

Additional numerous and varied compositions can be achieved by varying the first amount of material (2), the first capsule wall or coat (3), the second amount of material (5), the second capsule wall (6) or coat the carrier (10). The following non-limiting examples provide wash agents with a color changing carrier include:

The first amount of material (2) comprises citric acid, and wherein the first capsule wall (3) or coat comprises polyvinyl alcohol (Cevol 107), and wherein the second amount of material ( ) comprises bromophenol blue; and wherein the second capsule wall ( ) or coat comprises polyvinyl alcohol (Cevol 107), and wherein the carrier comprises a mixture of:
  a. an amount of polypropelene glycol (2000);
  b. an amount of Miracare MP35; and
  c. an amount of Tegosoft PSE 141G.

In this non-limiting example, the multiple zone capsule remains dormant until the addition of an amount of water and the second capsule wall degrades to release the indicator material (11) into the carrier (10) and the first capsule wall degrades to release the acid into the carrier (11). The acid acts to reduce pH of the carrier and the indicator material changes color.

The first amount of material (2) comprises citric acid, and wherein the first capsule wall (3) or coat comprises polyvinyl alcohol (Cevol 107), and wherein the second amount of material comprises bromophenol blue; and wherein the second capsule wall (6) or coat comprises polyvinyl alcohol (Cevol 107), and wherein the carrier (10) comprises a mixture of:
  a. an amount of polypropelene glycol (2000);
  b. an amount of Miracare MP35;
  c. an amount of Tegosoft PSE 141G; and
  d. an amount of sodium phosphate monobasic.

In this non-limiting example, the multiple zone capsule remains dormant until the addition of an amount of water and the second capsule wall degrades to release the indicator material (11) into the carrier (10) and the first capsule wall degrades to release the acid into the carrier (11). The acid acts to reduce pH of the carrier and the indicator material changes color and generates copious amounts of foam.

The first amount of material (2) comprises trisodium phosphate, and wherein the first coat comprises polyvinyl alcohol (Cevol 107), and wherein the second amount of material (5) comprises cresol red; and wherein the second capsule wall (6) comprises polyvinyl alcohol (Cevol 107), and wherein said carrier comprises a mixture of:
  a. an amount of polypropelene glycol (2000);
  b. an amount of Miracare MP35; and
  c. an amount of Tegosoft PSE 141G.

In this non-limiting example, the multiple zone capsule remains dormant until the addition of an amount of water and the second capsule wall degrades to release the indicator material (11) into the carrier (10) and the first capsule wall degrades to release the base into the carrier (11). The base acts to increase pH of the carrier and the indicator material changes color.

The first amount of material (3) comprises citric acid, and wherein the first capsule wall (3) or coat comprises polyvinyl alcohol (Cevol 107), wherein said second amount of material (5) comprises bromophenol blue; and wherein the second capsule wall (6) or coat comprises polyvinyl acetate-paraffin wax, and wherein the carrier comprises a mixture of:

a. an amount of water;
b. an amount of ammonium lauryl sulfate;
c. an amount of Silwet L-7220;
d. an amount of Tegosoft PSE 141G; and
e. an amount of sodium phosphate monobasic.

In this non-limiting example, the multiple zone capsule remains dormant until application of a sufficient amount of force ruptures the second capsule wall (6) to release the indicator material (11) into the carrier (10) and the first capsule wall degrades in response to water added to carrier to release the base into the carrier (11). The base acts to increase pH of the carrier and the indicator material changes color.

Each of the numerous and varied embodiments of the multiple zone material encapsulation and release system can be assigned to one of four broad categories. The first broad category and the second broad category comprises those embodiments of the multiple zone encapsulation and release system which comprise a first capsule wall (3) and a second capsule wall (6) which degrade in response to a second activation element and a first activation element which are the same (either the same chemical activation element or the same force application activation element) to release the second amount of material (5) and the first amount of material (2).

The third broad category of the multiple zone material encapsulation and release system invention comprises those embodiments having a second capsule wall (6) which releases the second amount of material in response to a second activation element comprising a chemical activation element and a first capsule wall (3) which releases the first amount of material (1) in response to a first activating element comprising a change in force upon the capsule.

The fourth broad category of the multiple zone material encapsulation and release system invention comprises those embodiments having the second capsule wall( ) which releases the second amount of material (6) in response to a second activating element comprising a change in force upon the second capsule wall (6) and having a first capsule wall (3) which releases the first amount of material (2) in response to a first activation element comprising a chemical activation element.

The following description of particular embodiments of the invention provide a sufficient number of examples of each of the single zone material encapsulation and release system and the multiple zone material encapsulation and release system to allow the manufacture and use of a numerous and varied embodiments of the invention encompassed by the generic descriptions above-provided and are not intended to be limiting with respect to the scope or breadth of the invention.

EXAMPLE 1

An amount of water soluble blue dye (although other colors can be used) can be encapsulated in the first zone by the use of vapor phase disposition. A dimer of para-xylene is vaporized by heating to about 175° C. at −1 torr. The vapor phase can then be pyrolyzed at about 660° C. and at about −0.5 torr to break the dimer into a pair reactive radicals. The pair of radicals are then applied to the surface of the dye where they react to form a poly(para-xylene) polymer thereby establishing a first capsule wall which bounds the first zone containing the amount of water soluble dye.

The resulting encapsulated dye is then added to alcohol. 1 gram of capsules is added to 2 grams of isopropanol. To this is added 0.5 grams of a water soluble yellow dye. When the dye is solubilized the solution is heated to 50° C. so that all the alcohol is removed. The resulting product is the original capsule containing the blue dye with the yellow dye absorbed or engaging the entirety of the outside surface of the first wall encapsulating the blue dye. The second zone of yellow dye can be similarly vapor phase coated, as described above.

0.1 grams of this particular embodiment of the multiple zone encapsulation system can be added to about 50 grams of an ethylene glycol carrier containing 1.5 grams dodecylether polyoxyethylene ethanol (12 moles) and 0.5 grams of disodium cocoamphodiacelate. A small portion of solution can be transferred to the surface of the hands for washing. When water is applied to the hands, foaming increases and after about 5-10 seconds the foam turns a light yellow. After about another 5-10 seconds, the foam turns green as a result of the blue dye being released and combining with the yellow dye.

EXAMPLE 2

First, 200 grams of a 10% solution (w/w) of gelatin are heated to about 40° C. and vigorously stirred. To this can be added about 2.0 grams of methylsalicylate. 110 grams of a 20% solution (w/w) of sodium sulfate are added to induce coacervation. The mixture can be cooled to 50° C. and 3 grams of glutaraldeyde are added to harden the gelatin. The pH is adjusted to 3.8. The procedure results in a first zone of methylsalicylate encapsulated by a first capsule wall which ruptures upon application of sufficient pressure.

Subsequently, 200 grams of a 10% solution (w/w) of gelatin are heated to 40° C. and vigorously stirred. About 1 gram of the microcapsules prepared as described above are added. 1.0 gram of 3-hydroxy methoxybenzaldehyde can be added followed by 110 grams of a 20% solution of sodium sulfate to induce coacervation. The mixture is cooled to 50° C. 3 grams of glutaraldehyde are added to harden the gelatin. The pH is adjusted to 4.0. The procedure results in a second zone of 3-hydroxy methoxybenzaldehyde encapsulated by a second capsule wall which ruptures in response to application of a sufficient amount of pressure.

0.1 gram of the multiple zone encapsulation system invention described above can be added to 50 grams of water containing 1.3 grams of sodium lauryl sulfate, 0.5 grams of disodiumcocoamphodiacetate. After gentle mixing, a portion of the composition can be transferred to the surface of the hands. Washing of the hands generates sufficient forces to rupture the second capsule wall releasing from the second zone 3-hydroxy-4-methoxybenzaldehyde after about 7 seconds generating a first fragrance of vanilla. After the elapse of about another 8 seconds, washing of the hands generates sufficient forces to rupture the first capsule wall releasing methylsalicylate contained in the first zone to provide a second fragrance of winter green.

EXAMPLE 3

In a manner similar to that described in Example 2, methylsalicylate encapsulated with a gelatin yields a first zone of material having a first capsule wall which ruptures in response to application of sufficient force. 1.0 gram of the capsules prepared as such can be added to 2 grams of isopropanol. To this 0.5 grams of a water soluble yellow dye can be added. The dye can be solubilized and the solution heated to about 50° C. until all alcohol is removed. The resulting material is encapsulated using vapor phase deposition as described in Example 1.

0.1 gram of the above-described capsule can be added to about 50 grams of ethylene glycol containing 1.5 grams of dodecylether polyoxyethylene ethanol (12 moles EO) and 0.5 grams of disodium cocoamphodiacetate to provide a carrier. A small portion of the composition can be transferred onto the surface of the hands for handwashing. When water is applied an almost immediate color change to yellow occurs. After an elapse of time of about 10 seconds and with continued rubbing, the light smell of wintergreen is generated.

EXAMPLE 4

In a manner similar to Example 1, a water soluble blue dye provides a first material containged in a first zone encapsulated using vapor phase deposition to provide a first capsule wall. 0.5 grams of the prepared capsules can be added to 100 grams of a 10% solution (w/w) of gelatin and are mixed gently so as not to rupture the capsules. 1.0 gram of methylsalicylate is added. 55 grams of a 20% (w/w) solution of sodium sulfate are added to induce coacervation. The mixture is cooled to 50° C.; 1.5 grams of glutaraldehyde are added to harden the gelatin. The pH is adjusted to 3.8. The resulting multiple zone capsule invention can be filtered, washed and dried.

About 0.1 gram of the above described multiple zone capsules are added to 50 grams of ethylene glycol containing 1.5 grams of dodecyletherpolyoxyethylene ethanol (12 moles EO) and 0.5 grams of disodium cocoamphodiacetate to provide a carrier. A small portion of the composition can be transferred to the surface of the hands for handwashing. Application of the forces generated during handwashing releases the methylsalicylate from the second zone providing a first fragrance of wintergreen. About 8 seconds after the addition of water (second activating environment) the composition on the surface of the hands turns a light blue due to the release of the dye from the first zone.

A large number of permutations and combinations of the multiple zone encapsulation invention can be made and used for handwashing compositions some of which are set out in Table 1 below.

TABLE 3

| | Zone 1 | Wall 1 | Zone 2 | Wall 2 |
|---|---|---|---|---|
| 1 | Color | Soluble | Color | Friable |
| 2 | Color | Soluble | Scent | Friable |
| 3 | Color | Friable | Color | Soluble |
| 4 | Color | Friable | Scent | Soluble |
| 5 | Scent | Soluble | Scent | Friable |
| 6 | Scent | Soluble | Color | Friable |
| 7 | Scent | Friable | Scent | Soluble |
| 8 | Scent | Friable | Color | Soluble |

EXAMPLE 5

A particle can be obtained by sizing citric acid crystals using a 200 mesh sieve. The particles collected after sizing are about ≤75μ. These particles can again be sieved through a 270 mesh sieve. That which passes through is discarded and those crystals remaining are now ≥53μ but ≤75μ. These crystals are placed in a Wuerster coating unit, or as is otherwise known as a fluid bed coater. Air rising from the bottom causes the crystals to be suspended and circulate in the chamber. Concurrently, volatilized polyvinyl alcohol previously dissolved in a water/alcohol solution is introduced. The polyvinyl alcohol can be a low molecular weight polymer (Mw=4000), which can be fully hydrolyzed. Such a polymer is commercially available from Celanese Corporation as Celvol 107. The coating process continues until the beads increase in size to about 70μ to 90μ. The beads are then removed from the coater as finished product.

A non-aqueous cleaning composition is prepared by mixing 50 grams of polypropylene glycol (2000), 5.0 grams of Miracare MP35, available from Rhodia, Inc., 1.0 gram of Tegosoft PSE141G, available from Goldschmidt Chemical Corp., 0.2 gram sodium phosphate monobasic, 0.02 gram of methyl orange, and 0.3 gram of the above described beads. The composition is gently blended so as not to rupture or otherwise disturb the beads. The composition has a very light yellow color due to the poor solubility of the sodium phosphate in a non-aqueous environment.

An effective amount of this composition is poured onto the hands. Rubbing begins along with the addition of a small amount of warm water. The foam becomes yellow immediately as the sodium phosphate dissolves. As the rubbing continues, capsule walls are slowly dissolved by the solvating action of the water. The carrier and other addenda lack sufficient polarity and solvating strength to dissolve the capsule walls in situ, thereby allowing for suitable shelf-life. When the citric acid crystals are exposed, they begin to dissolve. Prior to this event, the pH of the medium is about 4.5, which allows the methyl yellow to remain yellow. With the release of the acid, the pH drops to 3.1. This shift causes the methyl orange to change from yellow to red, due to the protonation of the dye molecule. The time required for the color change is about 35 seconds.

The wall thickness of the bead may be increased to adjust the time required for release of the citric acid into the carrier. Alternately, sodium phosphate monobasic can be encapsulated to mix with the citric acid into the carrier so as to create a change from red to yellow.

EXAMPLE 6

In like manner as described in Example 5, a bead can be prepared except that trisodium phosphate (12 moles of water) is similarly encapsulated. The carrier used can be the same with the exception of the elimination of sodium phosphate monobasic and the methyl orange being replaced with phenolphthalein. The pH of the carrier can be established as slightly acid at 6.5.

An effective amount of this composition is poured onto the hands. Rubbing begins along with the addition of a small amount of warm water. The foam remains clear. As the rubbing continues, the walls of the beads are slowly dissolved by the solvating action of the water. When the trisodium phosphate is exposed, it begins to dissolve. Prior to this event, the pH of the medium is about 6.5, which allows the phenolphthalein to remain clear. With the release of the basic trisodium phosphate, the pH increases to 10.1. This shift causes the phenolphthalein to change from clear to a vibrant red, due to the protonation of the dye molecule. The time required for the color change is about 30 seconds.

The capsule wall thickness of the bead may be increased to accordingly change the time required for release. Alternately, an acid such as citric, tartaric or ascorbic acid can be encapsulated to mix with trisodium phosphate, or other basic substance, in the carrier so as to create a change from red to clear.

EXAMPLE 7

In like manner as described in Example 5, a capsule is prepared except that trisodium phosphate (12 moles of water) is similarly encapsulated. The composition used can be the same with the exception of the addition of the same amount of sodium bicarbonate in lieu sodium phosphate monobasic and the methyl orange being replaced with phenol violet. The pH of the carrier can be established as slightly acid at 6.5 and the addition of the sodium bicarbonate makes the carrier a very light yellow.

An effective amount of this composition is poured onto the hands. Rubbing begins along with the addition of a small amount of warm water. The foam turns a stronger yellow as the sodium bicarbonate is dissolved. As the rubbing continues, the capsule walls slowly dissolve by the solvating action of the water. When the trisodium phosphate is exposed, it begins to dissolve. Prior to this event, the pH of the medium is about 8.2, which allows the phenol violet to impart an intense yellow color. With the release of the basic trisodium phosphate, the pH increases to 10.6. This shift causes the phenol violet to change from yellow to a violet, due to the protonation of the dye molecule. The time required for the color change is about 38 seconds.

Again, the capsule wall thickness of the bead may be increased to accordingly change the time required for release. Alternately, a weak base such as the sodium bicarbonate can be encapsulated to mix with the trisodium phosphate, or a stronger base, into the composition so as to create a change from violet to yellow.

EXAMPLE 8

A capsule can be prepared by sizing citric acid crystals using a 200 mesh sieve. The particles collected after sizing are all ≤75μ. This material is again sieved through a 270 mesh sieve. That which passes through is discarded and those crystals remaining are now ≥53μ but ≤75μ. These crystals are placed in a Wuerster coating unit, or as is otherwise known as a fluid bed coater. Air rising from the bottom causes the crystals to be suspended and circulate in the chamber. Concurrently, volatilized polyvinyl acetate/paraffin wax previously dissolved in a xylene/methoxy ethanol solution is introduced. The polyvinyl acetate is a medium molecular weight polymer (Mw=83,000) and has a Ford No. 4 viscosity @ 25° C. of 13-14.5 sec. The paraffin wax has a melt range of 73°-80° C. The coating process continues until the beads increase in size to about 75 to 100μ. The beads are then removed from the coater as finished product.

An aqueous cleaning composition is prepared by mixing 50 grams of deionized water, 5.7 grams of ammonium lauryl sulfate (70%), Silwet L-7220, available from Rhodia, Inc., 1.0 gram of Tegosoft PSE141G, available from Osi Specialties, 0.2 gram sodium phosphate monobasic, 0.02 gram of methyl orange, and 0.3 gram of the above described beads. The composition is gently blended so as not to rupture or otherwise disturb the beads. The composition has a very distinct yellow color. This is in contrast to Example 1 wherein the sodium phosphate was not dissolved but dispersed. In an aqueous medium, the dissolution of the phosphate salt permits the pH indicator to become a strong yellow.

An effective amount of this composition is poured onto the hands. Rubbing begins along with the addition of a small amount of warm water. The foam is yellow. As the rubbing continues, the walls of the beads are slowly ruptured by the mechanical action of washing. Prior to this event, the pH of the medium is about 4.5, which allows the methyl yellow to remain yellow. With the release of the citric acid, the pH drops to 3.1. This shift causes the methyl orange to change from yellow to red, due to the protonation of the dye molecule. The time required for the color change is about 24 seconds.

EXAMPLE 9

In like manner as described in Example 8, a capsule can be prepared except that trisodium phosphate (12 moles of water) is similarly encapsulated. The composition used is the same with the exception of the methyl orange being replaced with phenolphthalein. The pH of the carrier is slightly acid at 4.5 due to the complete dissolution of the sodium phosphate monobasic.

An effective amount of this composition is poured onto the hands. Rubbing begins along with the addition of a small amount of warm water. The foam remains clear due to the acid nature of the composition. As the rubbing continues, the walls of the beads are ruptured by the mechanical action of washing. When the trisodium phosphate is exposed, it begins to dissolve. Prior to this event, the pH of the medium is about 4.5, which allows the phenolphthalein to remain clear. With the release of the basic trisodium phosphate, the pH increases to 9.7. This shift causes the phenolphthalein to change from clear to a vibrant red, due to the protonation of the dye molecule. The time required for the color change is about 32 seconds.

The capsule wall thickness of the capsule may be increased to accordingly change the time required for release. Alternately, an acid such as citric, tartaric, ascorbic acid, or the salt of an acid can be encapsulted to mix the trisodium phosphate, or other basic substance, in the aqueous carrier so as to create a change from red to clear.

EXAMPLE 10

In like manner as described in Example 5, a capsule can be prepared except that trisodium phosphate (12 moles of water) is similarly encapsulated. The composition used is the same with the exception of the addition of the same amount of sodium bicarbonate in lieu sodium phosphate monobasic and the methyl orange being replaced with phenol violet. The pH of the carrier is slightly alkaline at 8.2 and the addition of the sodium bicarbonate makes the solution an intense yellow.

An effective amount of this composition is poured onto the hands. Rubbing begins along with the addition of a small amount of warm water. The foam is immediately a bright yellow. As the rubbing continues, the walls of the beads are ruptured through the mechanical action of washing. When the trisodium phosphate is exposed, it begins to dissolve. Prior to this event, the pH of the medium is about 8.2, which allows the phenol violet to impart an intense yellow color. With the release of the basic trisodium phosphate, the pH increases to 10.6. This shift causes the phenol violet to change from yellow to a violet, due to the protonation of the dye molecule. The time required for the color change is about 29 seconds.

The capsule wall thickness can be increased to accordingly change the time required for release. Alternately, a weak base such as the sodium bicarbonate can be encapsuled to mix the trisodium phosphate, or a stronger base, in the carrier so as to create a change from violet to yellow.

EXAMPLE 11

Capsules can be prepared wherein methyl salicylate is encapsulated. This is accomplished using a process known as coacervation. Coacervation takes advantage of the immiscibility of various substances in water. In the present instance, methyl salicylate, or as it is also known, oil of wintergreen, is added to water. With high speed shear mixing, the methyl salicylate is broken into smaller droplets, but yet is never emulsified. Gelatin is added to the mixing dispersion wherein the gelatin dissolves in water and is then adsorbed onto the surface of the methyl salicylate droplets by saturating the solution with a spectator salt, and pushing the gelatin out of solution. While still mixing, glutaraldehyde is added to harden or cross-link the gelatin since it would lack sufficient integrity to remain in tact otherwise. With the addition of the aldehyde complete, the mixing is stopped and the beads are removed, filtered and washed.

A non-aqueous cleaning composition is prepared by mixing 50 grams of polyethylene glycol (600), 7.0 grams of Igepal CO-880, available from Rhodia, Inc., 2.0 grams of Surfonic DDA-12, available from Huntsman Corp., and 0.5 gram of the above described beads. The composition is gently blended so as not to rupture or otherwise disturb the beads. The composition is clear and has no discernable odor.

An effective amount of this composition is poured onto the hands. Rubbing begins along with the addition of a small amount of warm water. Foam is generated immediately with no other noticeable result. As the rubbing continues, the walls of the beads are ruptured due to the mechanical action of washing. After approximately 25 seconds, there is a detectable odor of oil of wintergreen.

EXAMPLE 12

In like manner as described in Example 7, beads are prepared except that methyl salicylate is substituted with 3-methoxy-4-hydroxy benzaldehyde (vanillin). This is similarly accomplished using coacervation with gelatin and hardening with glutaraldehyde.

An aqueous cleaning composition is prepared by mixing 50 grams of deionized water, 5.0 grams of sodium octyl sulfate, 0.6 gram of sodium dodecyl benzene sulfonate, and 0.7 gram of the above described beads. The composition is gently blended so as not to rupture or otherwise disturb the beads. The composition is clear and has no discernable odor.

An effective amount of this composition is poured onto the hands. Rubbing begins along with the addition of a small amount of warm water. Foam is generated immediately with no other noticeable result. As the rubbing continues, the walls of the beads are ruptured due to the mechanical action of washing. After approximately 22 seconds, there is a detectable odor of vanilla.

EXAMPLE 13

A capsule can be prepared by sizing sugar crystals using a 170 mesh sieve. The particles collected after sizing are all ≤90μ. This material is again sieved through a 230 mesh sieve. That which passes through is discarded and those crystals remaining are now ≥63μ but ≤90μ. These crystals are placed in a Wuerster coating unit, or as is otherwise known as a fluid bed coater. Air rising from the bottom causes the crystals to be suspended and circulate in the chamber. Concurrently, volatilized blue dye, previously dissolved in a water solution is introduced. The dye is water soluble blue dye #7. The coating process continues until the beads increase in size to about 100 to 130μ. At this point the dye solution is removed and replace with the same polyvinyl alcohol solution as described in Example 5. The dye coated beads are then further coated with the polyvinyl alcohol to provide a protective layer. The coating process continues until the beads increase in size to about 125 to 160μ. The beads are then removed from the coater as finished product.

A non-aqueous cleaning composition is prepared by mixing 50 grams of polypropylene glycol (2000), 5.0 grams of Miracare MP35, available from Rhodia, Inc., 1.0 gram of Tegosoft PSE141G, available from Goldschmidt Chemical Corp., and 0.6 gram of the above described beads. The composition is gently blended so as not to rupture or otherwise disturb the beads. The composition is clear and has no color.

An effective amount of this composition is poured onto the hands. Rubbing begins along with the addition of a small amount of warm water. The composition foams but remains as white foam. As the rubbing continues, the walls of the beads are slowly dissolved by the solvating action of the water. As the polyvinyl alcohol is removed and exposes the dye, the dye immediately dissolves and imparts a distinct color shift from white to blue. The time required for the color change is about 38 seconds.

Capsule wall thickness can be increased to accordingly change the time required for release.

EXAMPLE 14

A capsule can be prepared by sizing sugar crystals using a 170 mesh sieve. The particles collected after sizing are ≤90μ. This material is again sieved through a 230 mesh sieve. That which passes through is discarded and those crystals remaining are now ≥63μ but ≤90μ. These crystals are placed in a Wuerster coating unit, or as is otherwise known as a fluid bed coater. Air rising from the bottom causes the crystals to be suspended and circulate in the chamber. Concurrently, volatilized blue dye, previously dissolved in a water solution is introduced. The dye is water soluble blue dye #7. The coating process continues until the beads increase in size to about 100 to 130μ. At this point the dye solution is removed and replace with the same polyvinyl acetate/paraffin wax solution as described in Example 4. The dye coated beads are then further coated with the polyvinyl acetate/wax combination to provide a protective layer. The coating process continues until the beads increase in size to about 125 to 160μ. The beads are then removed from the coater as finished product.

An aqueous cleaning composition is prepared by mixing 50 grams of deionized water, 5.7 grams of ammonium lauryl sulfate (70%), Silwet L-7220, available from Rhodia, Inc., 1.0 gram of Tegosoft PSE141G, available from OSi Specialties, and 0.6 gram of the above described beads. The composition is gently blended so as not to rupture or otherwise disturb the beads. The composition has a very distinct yellow color.

An effective amount of this composition is poured onto the hands. Rubbing begins along with the addition of a small amount of warm water. The foam is initially white. As the rubbing continues, the walls of the beads are slowly ruptured by the mechanical action of washing. The foam changes quickly from clear to blue. The time required for the color change is about 32 seconds.

EXAMPLE 15

A capsule can be prepared by sizing citric acid crystals using a 200 mesh sieve. The particles collected after sizing are all ≤75μ. This material is again sieved through a 270 mesh sieve. That which passes through is discarded and those crystals remaining are now ≥53μ but ≤75μ. These crystals are placed in a Wuerster coating unit, or as is otherwise known as a fluid bed coater. Air rising from the bottom causes the crystals to be suspended and circulate in the chamber. Concurrently, volatilized polyvinyl alcohol previously dissolved in a water/alcohol solution is introduced. The polyvinyl alcohol is a low molecular weight polymer (Mw=4000), which is fully hydrolyzed. Such a polymer is commercially available from Celanese Corporation as Celvol 107. The coating process continues until the beads increase in size to about 70μ to 90μ. The beads are then removed from the coater as finished product.

A non-aqueous cleaning composition is prepared by mixing 50 grams of polypropylene glycol (2000), 5.0 grams of Miracare MP35, available from Rhodia, Inc., 1.0 gram of Tegosoft PSE141G, available from Goldschmidt Chemical Corp., 0.2 gram sodium sodium bicarbonate, and 0.3 gram of the above described beads. The composition is gently blended so as not to rupture or otherwise disturb the beads.

An effective amount of this composition is poured onto the hands. Rubbing begins along with the addition of a small amount of warm water. As the rubbing continues, the walls of the beads are slowly dissolved by the solvating action of the water. When the citric acid crystals are exposed, they begin to dissolve. Prior to this event, the pH of the medium is about 8.2. With the release of the acid, the pH drops to 3.1. This shift causes the sodium bicarbonate to react with the citric acid. The double displacement reaction liberates carbon dioxide. The rapid release of $CO_2$ causes the foam to effervesce, which is both visible and audible. The time required for the effect to occur is about 24 seconds.

Capsule wall thickness can be increased to accordingly change the time required for release.

EXAMPLE 16

A capsule can be prepared by sizing citric acid crystals using a 200 mesh sieve. The particles collected after sizing are all ≤75μ. This material is again sieved through a 270 mesh sieve. That which passes through is discarded and those crystals remaining are now ≥53μ but ≤75μ. These crystals are placed in a Wuerster coating unit, or as is otherwise known as a fluid bed coater. Air rising from the bottom causes the crystals to be suspended and circulate in the chamber. Concurrently, volatilized polyvinyl acetate/paraffin wax previously dissolved in a xylene/methoxy ethanol solution is introduced. The polyvinyl acetate is a medium molecular weight polymer (Mw=83,000) and has a Ford No. 4 viscosity @ 25° C. of 13-14.5 sec. The paraffin wax has a melt range of 73°-80° C. The coating process continues until the beads increase in size to about 75 to 100 μl. The beads are then removed from the coater as finished product.

An aqueous cleaning composition is prepared by mixing 50 grams of deionized water, 5.7 grams of ammonium lauryl sulfate (70%), Silwet L-7220, available from Rhodia, Inc., 1.0 gram of Tegosoft PSE141G, available from Osi Specialties, 0.2 gram sodium bicarbonate, and 0.3 gram of the above described beads. The composition is gently blended so as not to rupture or otherwise disturb the beads.

An effective amount of this composition is poured onto the hands. Rubbing begins along with the addition of a small amount of warm water. The foam is white. As the rubbing continues, the walls of the beads are slowly ruptured by the mechanical action of washing. Prior to this event, the pH of the medium is about 8.2. With the release of the citric acid, the pH drops to 3.1. This shift causes the sodium bicarbonate to react with the citric acid. The double displacement reaction liberates carbon dioxide. The rapid release of $CO_2$ causes the foam to effervesce, which is both visible and audible. The time required for the effect to occur is about 22 seconds.

EXAMPLE 17

A capsule can be prepared by sizing citric acid crystals using a 200 mesh sieve. The particles collected after sizing are all ≤75μ. This material is again sieved through a 270 mesh sieve. That which passes through is discarded and those crystals remaining are now ≥53μ but ≤75μ. These crystals are placed in a Wuerster coating unit, or as is otherwise known as a fluid bed coater. Air rising from the bottom causes the crystals to be suspended and circulate in the chamber. Concurrently, volatilized polyvinyl alcohol previously dissolved in a water/alcohol solution is introduced. The polyvinyl alcohol is a low molecular weight polymer (Mw=4000), which is fully hydrolyzed. Such a polymer is commercially available from Celanese Corporation as Celvol 107. The coating process continues until the beads increase in size to about 70 to 90μ. The polyvinyl alcohol solution is removed and replaced with a 30% aqueous solution of bromphenol blue. The same beads are coated again with the pH dye indicator until reaching a bead size of 75μ to 95μ. Finally, the bromphenol blue solution is removed and replaced with the same polyvinyl alcohol solution described above. The coating process continues until the beads are coated to an increased and final size of 90μ to 115μ. The beads are then removed from the coater.

In like manner as described in Example 5, a non-aqueous cleaning composition is prepared by mixing 50 grams of polypropylene glycol (2000), 5.0 grams of Miracare MP35, available from Rhodia, Inc., 1.0 gram of Tegosoft PSE141G, available from Goldschmidt Chemical Corp., 0.2 gram sodium phosphate monobasic, and 0.7 gram of the above described beads. The composition is gently blended so as not to rupture or otherwise disturb the beads. The composition is completely clear since there is no dye in the carrier, but rather encapsulated in the heretofore described bead.

An effective amount of this composition is poured onto the hands. Rubbing begins along with the addition of a small amount of warm water. The foam is initially white. The sodium phosphate monobasic dissolves. As the rubbing continues, the walls of the beads are slowly dissolved by the solvating action of the water. The carrier and other addenda lack sufficient polarity and solvating strength to do so in situ, thereby allowing for suitable shelf-life. The bromphenol blue is released initially thereby causing the foam to turn blue. This requires about 8 seconds. As the rubbing continues, the second layer of polyvinyl alcohol is dissolved. When the citric acid crystal are exposed, they begin to dissolve. Prior to this event, the pH of the medium is about 4.4, which allows the bromphenol blue to remain blue. With the release of the acid, the pH drops to 3.2. This shift causes the bromphenol blue to change from blue to yellow, due to the protonation of the dye molecule. The time required for the color change is about 38 seconds.

Capsule wall thickness of the bead may be increased to accordingly change the time required for release. Alternately, sodium phosphate monobasic can be encapsuled to mix with citric acid in the carrier so as to create a change from yellow to blue.

EXAMPLE 18

In like manner as described in Example 17, a capsule can be prepared except that trisodium phosphate (12 moles of water) is similarly encapsulated in lieu of the citric acid. Similarly, the bead is coated with cresol red in place of phenolphthalein.

This is likewise coated with polyvinyl alcohol. The pH of the carrier is slightly acid at 6.5 and therefore needs no agent to create an acid environment.

An effective amount of this composition is poured onto the hands. Rubbing begins along with the addition of a small amount of warm water. The foam remains clear. As the rubbing continues, the walls of the beads are slowly dissolved by the solvating action of the water. When the cresol red is exposed, it immediately turns the foam yellow. The time required is about 6 seconds. The second layer of polyvinyl alcohol begins to dissolve. When the trisodium phosphate is exposed, it is solubilized. Prior to this event, the pH of the medium is about 6.5, which allows the cresol red to remain yellow. With the release of the basic trisodium phosphate, the pH increases to 10.1. This shift causes the cresol red to change from yellow to purple, due to the protonation of the dye molecule. The time required for the second color change is about 34 seconds.

Capsule wall thickness can be increased to accordingly change the time required for release. It is also evident that one may encapsulate an acid such as citric, tartaric or ascorbic acid and mix the trisodium phosphate, or other basic substance, into the composition so as to create a change from purple to yellow. This example demonstrates a color change using and acid-to-base shift in pH.

EXAMPLE 19

In like manner as described in Example 18, a capsule can be prepared except that trisodium phosphate (12 moles of water) is similarly encapsulated. The capsules thus formed are then coated with a 30% aqueous solution of thymolphthalein such that the beads are about 75μ to 95μ in diameter. The beads are finally coated with the original polyvinyl alcohol solution so that the average size is in the range of 90μ to 115μ. The composition used is the same with the exception of the addition of the same amount of sodium bicarbonate in lieu sodium phosphate monobasic. The pH of the carrier is slightly basic at 8.2.

An effective amount of this composition is poured onto the hands. Rubbing begins along with the addition of a small amount of warm water. The foam is initially white. As the rubbing continues, the walls of the beads are slowly dissolved by the solvating action of the water. When the thymolphthalein is released, the solution continues to remain white since at a pH of 8.2, thymolphthalein is colorless. When the trisodium phosphate is exposed as the rubbing action continues, it begins to dissolve. Prior to this event, the pH of the medium is about 8.2, which again favors the thymolphthalein to remain clear. With the release of the basic trisodium phosphate, the pH increases to 10.6. This shift causes the thymolphthalein to change from clear to blue, due to the protonation of the dye molecule. The time required for the color change is about 29 seconds.

The capsule wall thickness can be increased to accordingly change the time required for release. Alternately, a weak base such as the sodium bicarbonate can be encapsulated to mix trisodium phosphate, or a stronger base, in the carrier so as to create a change from blue to clear. This example demonstrates a color change using and base-to-base shift in pH.

EXAMPLE 20

In like manner as described in Example 17, a capsule can be prepared with the sole exception being that the second application of poly vinyl alcohol is replaced with the solvent based mixture of polyvinyl acetate and paraffin wax. The resulting bead is therefore citric acid coated with polyvinyl alcohol. This is then coated with bromphenol blue and finally with the heretofore described mixture of polyvinyl acetate and paraffin wax.

An aqueous cleaning composition is prepared by mixing 50 grams of deionized water, 5.7 grams of ammonium lauryl sulfate (70%), Silwet L-7220, available from Rhodia, Inc., 1.0 gram of Tegosoft PSE141G, available from Osi Specialties, 0.2 gram sodium phosphate monobasic, and 0.7 gram of the above described beads. The composition is gently blended so as not to rupture or otherwise disturb the beads. The composition is colorless. Since the pH indicator dye is encapsulated, and although the sodium phosphate is fully dissolved, there is no color imparted.

An effective amount of this composition is poured onto the hands. Rubbing begins along with the addition of a small amount of warm water. The foam is initially white. The sodium phosphate monobasic dissolves. As the rubbing continues, the walls of the beads are slowly ruptured by the mechanical action of washing. The bromphenol blue is released initially thereby causing the foam to turn blue. This requires about 7 seconds. As the rubbing continues, the second layer of polyvinyl alcohol is dissolved. When the citric acid crystal are exposed, they begin to dissolve. Prior to this event, the pH of the medium is about 4.4, which allows the bromphenol blue to remain blue. With the release of the acid, the pH drops to 3.2. This shift causes the bromphenol blue to change from blue to yellow, due to the protonation of the dye molecule. The time required for the color change is about 38 seconds.

Capsule wall thickness can be increased to accordingly change the time required for release. Alternately, the sodium phosphate monobasic can be encapsulated to mix with the citric acid in the carrier so as to create a change from yellow to blue.

EXAMPLE 21

In like manner as described in Example 20, a capsule can be prepared except that trisodium phosphate (12 moles of water) is similarly encapsulated in lieu of the citric acid. Similarly, the bead is coated with cresol red in place of phenolphthalein. The difference is that the bead is then coated with a solvent based mixture of polyvinyl acetate and paraffin wax. The pH of the carrier is slightly acid at 6.5 and therefore needs no agent to create an acid environment.

An effective amount of this composition is poured onto the hands. Rubbing begins along with the addition of a small amount of warm water. The foam remains clear. As the rubbing continues, the walls of the beads are slowly ruptured by the mechanical action of washing. When the cresol red is exposed, it immediately turns the foam yellow. The time required is about 6 seconds. The second layer of polyvinyl alcohol begins to dissolve. When the trisodium phosphate is exposed, it is solubilized. Prior to this event, the pH of the medium is about 6.5, which allows the cresol red to remain yellow. With the release of the basic trisodium phosphate, the pH increases to 10.1. This shift causes the cresol red to change from yellow to purple, due to the protonation of the dye molecule. The time required for the second color change is about 34 seconds.

Capsule wall thickness of the bead may be increased to accordingly change the time required for release. Alternately, an acid such as citric, tartaric or ascorbic acid an be encapsulated and mix the trisodium phosphate, or other basic substance, into the composition so as to create a change from purple to yellow.

EXAMPLE 22

In like manner as described in Example 19, a capsule can be prepared except that trisodium phosphate (12 moles of water) is similarly encapsulated. The capsule thus formed are then coated with a 30% aqueous solution of thymolphthalein such that the beads are about 75 to 95μ in diameter. The difference is now that the capsules are coated with the heretofore described solvent solution of polyvinyl acetate and paraffin wax so that the average size is in the range of 90μ to 115μ. The composition used is the same with the exception of the addition of the same amount of sodium bicarbonate in lieu sodium phosphate monobasic. The pH of the carrier is slightly basic at 8.2.

An effective amount of this composition is poured onto the hands. Rubbing begins along with the addition of a small amount of warm water. The foam is initially white. As the rubbing continues, the walls of the beads are slowly ruptured by the mechanical action of washing. When the thymolphthalein is released, the solution continues to remain white since at a pH of 8.2, thymolphthalein is colorless. When the trisodium phosphate is exposed as the rubbing action continues, it begins to dissolve. Prior to this event, the pH of the medium is about 8.2, which again favors the thymolphthalein to remain clear. With the release of the basic trisodium phosphate, the pH increases to 10.6. This shift causes the thymolphthalein to change from clear to blue, due to the protonation of the dye molecule. The time required for the color change is about 29 seconds.

Capsule wall thickness can be increased to accordingly change the time required for release. Alternately, a weak base such as the sodium bicarbonate can be encapsulated to mix with the trisodium phosphate, or a stronger base, in the carrier so as to create a change from blue to clear. This example demonstrates a color change using and base-to-base shift in pH.

EXAMPLE 23

In lice manner as described in Example 11, capsules are prepared with methyl salicylate encapsulated. The prepared capsules are then placed in a fluid bead coater and coated with a 30% aqueous solution of blue dye. These coated beads are then subsequently coated with polyvinyl alcohol as described in Example 5. This results in a multi-walled bead wherein the outside is polyvinyl alcohol with a dye underneath. Then there is a hard gelatin layer containing methyl salicylate.

A non-aqueous cleaning composition is prepared by mixing 50 grams of polypropylene glycol (2000), 5.0 grams of Miracare MP35, available from Rhodia, Inc., 1.0 gram of Tegosoft PSE141G, available from Goldschmidt Chemical Corp., and 1.0 gram of the above described beads. The composition is gently blended so as not to rupture or otherwise disturb the beads. The composition is completely clear since there is no dye in the carrier, but rather encapsulated in the heretofore described bead.

An effective amount of this composition is poured onto the hands. Rubbing begins along with the addition of a small amount of warm water. The foam is initially white. As the rubbing continues, the walls of the beads are slowly dissolved by the solvating action of the water. The blue dye is released thereby causing the foam to turn blue. This requires about 5 seconds. As the rubbing continues, the second layer of gelatin is ruptured through the mechanical action of rubbing. When the methyl salicylate is released, the distinct smell of oil of wintergreen is detected. The time required for the color change is about 32 seconds.

EXAMPLE 24

A capsule can be prepared by sizing sugar crystals using a 170 mesh sieve. The particles collected after sizing are all ≤90μ. This material is again sieved through a 230 mesh sieve. That which passes through is discarded and those crystals remaining are now ≥63μ but ≤90μ. These crystals are placed in a Wuerster coating unit, or as is otherwise known as a fluid bed coater. Air rising from the bottom causes the crystals to be suspended and circulate in the chamber. Concurrently, volatilized blue dye, previously dissolved in a water solution is introduced. The dye is water soluble blue dye #7. The coating process continues until the capsules or beads increase in size to about 100 to 130μ. At this point the dye solution is removed and replace with the same polyvinyl alcohol solution as described in Example 1. The dye coated capsules or beads are then further coated with the polyvinyl alcohol to provide a protective layer. The coating process continues until the capsules increase in size to about 125 to 160μ. A 30% solution of a yellow dye is then coated onto the beads already formed so that the size range is between about 140 and 1801μ. Finally, these beads are again coated with polyvinyl alcohol as described above to a finished size range of about 165 and 200μ. Therefore, a multi-walled bead is realized that is coated on the outside with polyvinyl alcohol protecting a yellow dye underneath. Below this is another layer of polyvinyl alcohol protecting a blue dye underneath. The beads are then removed from the coating unit.

A non-aqueous cleaning composition is prepared by mixing 50 grams of polypropylene glycol (2000), 5.0 grams of Miracare MP35, available from Rhodia, Inc., 1.0 gram of Tegosoft PSE141G, available from Goldschmidt Chemical Corp., and 1.2 grams of the above described beads. The composition is gently blended so as not to rupture or otherwise disturb the beads. The composition is clear and has no color.

An effective amount of this composition is poured onto the hands. Rubbing begins along with the addition of a small amount of warm water. The composition foams but remains as white foam. As the rubbing continues, the walls of the beads are slowly dissolved by the solvating action of the water. As the polyvinyl alcohol is removed and exposes the dye, the dye immediately dissolves and imparts a distinct color shift from white to yellow. The time required for the initial color change is about 7 seconds. As the rubbing continues, the next layer of polyvinyl alcohol dissolves thereby releasing the blue dye. The foam changes from yellow to green when the two dyes interact. The time required for the second color change is about 33 seconds.

Capsule wall thickness can be increased to accordingly change the time required for release.

EXAMPLE 25

A capsule can be prepared by sizing sugar crystals using a 170 mesh sieve. The particles collected after sizing are all ≤90μ. This material is again sieved through a 230 mesh sieve. That which passes through is discarded and those crystals remaining are now ≥63μ but ≤90μ. These crystals are placed in a Wuerster coating unit, or as is otherwise known as a fluid bed coater. Air rising from the bottom causes the crystals to be suspended and circulate in the chamber. Concurrently, volatilized blue dye, previously dissolved in a water solution is introduced. The dye is water soluble blue dye #7. The coating process continues until the beads increase in size to about 100 to 130µ. At this point the dye solution is removed and replaced with the same polyvinyl alcohol solution as described in Example 1. The dye coated beads are then further coated with the polyvinyl alcohol to provide a protective layer. The coating process continues until the beads increase in size to about 125 to 160µ. A 25% solution of sodium acetate is then coated onto the beads already formed so that the size range is between about 140 and 180µ. Finally, these beads are again coated with polyvinyl alcohol as heretofore described to a finished size range of about 165 and 200µ. Therefore, a multi-walled bead is realized that is coated on the outside with polyvinyl alcohol protecting sodium acetate underneath. Below this is layer of polyvinyl alcohol protecting a blue dye underneath. The beads are then removed from the coating unit.

A non-aqueous cleaning composition is prepared by mixing 50 grams of polypropylene glycol (2000), 5.0 grams of Miracare MP35, available from Rhodia, Inc., 1.0 gram of Tegosoft PSE141G, available from Goldschmidt Chemical Corp., 0.6 gram sodium carbonate, and 1.2 grams of the above described beads. The composition is gently blended so as not to rupture or otherwise disturb the beads. The composition is clear and has no color.

An effective amount of this composition is poured onto the hands. Rubbing begins along with the addition of a small amount of warm water. The composition foams but remains as white foam. As the rubbing continues, the protective layer of polyvinyl alcohol dissolves thereby exposing the sodium acetate. When the sodium acetate interacts with the already dissolved sodium carbonate, there is a double displacement reaction resulting in the release of carbon dioxide gas. This effervescence causes the foam to lather even more. The time for this release is about 7 seconds. As the rubbing continues, the second layer of polyvinyl alcohol dissolves thereby releasing the dye. It immediately turns the foam blue. The time required for this action is about 29 seconds.

EXAMPLE 26

In like manner as described in Example 11, capsules can be prepared with methyl salicylate encapsulated. The prepared beads are then placed in a fluid bead coater and coated with a 30% aqueous solution of blue dye. These coated beads are then subsequently coated with polyvinyl acetate/paraffin wax as described in Example 4. This results in a multi-walled bead wherein the outside is polyvinyl alcohol with a dye underneath. Then there is a hard gelatin layer containing methyl salicylate.

An aqueous cleaning composition is prepared by mixing 50 grams of deionized water, 5.7 grams of ammonium lauryl sulfate (70%), Silwet L-7220, available from Rhodia, Inc., 1.0 gram of Tegosoft PSE141G, available from Osi Specialties, and 1.2 grams of the above described beads. The composition is gently blended so as not to rupture or otherwise disturb the beads. The composition is colorless and odorless.

An effective amount of this composition is poured onto the hands. Rubbing begins along with the addition of a small amount of warm water. The foam is initially white. As the rubbing continues, the walls of the beads are slowly dissolved by the solvating action of the water. The blue dye is released initially thereby causing the foam to turn blue. This requires about 5 seconds. As the rubbing continues, the second layer of gelatin is ruptured through the mechanical action of rubbing. When the methyl salicylate is released, the distinct smell of oil of wintergreen is detected. The time required for the color change is about 32 seconds.

EXAMPLE 27

A capsule can be prepared by sizing sugar crystals using a 170 mesh sieve. The particles collected after sizing are all ≤90µ. This material is again sieved through a 230 mesh sieve. That which passes through is discarded and those crystals remaining are now ≥63µ but ≤90µ. These crystals are placed in a Wuerster coating unit, or as is otherwise known as a fluid bed coater. Air rising from the bottom causes the crystals to be suspended and circulate in the chamber. Concurrently, volatilized blue dye, previously dissolved in a water solution is introduced. The dye is water soluble blue dye #7. The coating process continues until the beads increase in size to about 100 to 130µ. At this point the dye solution is removed and replace with the same polyvinyl alcohol solution as described in Example 5. The dye coated beads are then further coated with the polyvinyl alcohol to provide a protective layer. The coating process continues until the beads increase in size to about 125 to 160µ. A 30% solution of a yellow dye is then coated onto the beads already formed so that the size range is between about 140 and 180µ. Finally, these beads are again coated with polyvinyl acetate/paraffin wax composition as described in Example 4 to a finished size range of about 165 and 200µ. Therefore, a multi-walled bead is realized that is coated on the outside with polyvinyl acetate and paraffin wax protecting a yellow dye underneath. Below this is layer of polyvinyl alcohol protecting a blue dye underneath. The beads are then removed from the coating unit.

An aqueous cleaning composition is prepared by mixing 50 grams of deionized water, 5.7 grams of ammonium lauryl sulfate (70%), Silwet L-7220, available from Rhodia, Inc., 1.0 gram of Tegosoft PSE141G, available from Osi Specialties, and 1.2 grams of the above described beads.

An effective amount of this composition is poured onto the hands. Rubbing begins along with the addition of a small amount of warm water. The composition foams but remains as white foam. As the rubbing continues, the walls of the beads are ruptured by the mechanical action of washing. As the polyvinyl acetate/wax layer is removed, the dye immediately dissolves and imparts a distinct color shift from white to yellow. The time required for the initial color change is about 9 seconds. As the rubbing continues, the next layer of polyvinyl alcohol dissolves thereby releasing the blue dye. The foam changes from yellow to green when the two dyes interact. The time required for the second color change is about 36 seconds.

Capsule wall thickness of the bead may be increased to accordingly change the time required for release.

EXAMPLE 28

A capsule can be prepared by sizing sugar crystals using a 170 mesh sieve. The particles collected after sizing are all ≤90µ. This material is again sieved through a 230 mesh sieve. That which passes through is discarded and those crystals remaining are now ≥63µ but ≤90µ. These crystals are placed in a Wuerster coating unit, or as is otherwise known as a fluid bed coater. Air rising from the bottom causes the crystals to be suspended and circulate in the chamber. Concurrently, volatilized blue dye, previously dissolved in a water solution is introduced. The dye is water soluble blue dye #7. The coating process continues until the beads increase in size to about 100 to 130µ. At this point the dye solution is removed and replaced with the same polyvinyl alcohol solution as described in Example 1. The dye coated beads are then further coated with the polyvinyl alcohol to provide a protective layer. The coating process continues until the beads increase in size to about 125 to 160μ. A 25% solution of sodium acetate is then coated onto the beads already formed so that the size range is between about 140 and 180μ. Finally, these beads are again coated with polyvinyl acetate/paraffin wax composition as described in Example 8 to a finished size range of about 165 and 200μ. Therefore, a multi-walled bead is realized that is coated on the outside with polyvinyl acetate and paraffin wax protecting a yellow dye underneath. Below this is layer of polyvinyl alcohol protecting a blue dye underneath. The beads are then removed from the coating unit.

An aqueous cleaning composition is prepared by mixing 50 grams of deionized water, 5.7 grams of ammonium lauryl sulfate (70%), Silwet L-7220, available from Rhodia, Inc., 1.0 gram of Tegosoft PSE141G, available from Osi Specialties, and 1.2 grams of the above described beads.

An effective amount of this composition is poured onto the hands. Rubbing begins along with the addition of a small amount of warm water. The composition foams but remains as white foam. As the rubbing continues, the protective layer of polyvinyl acetate/wax ruptures thereby exposing the sodium acetate. When the sodium acetate interacts with the already dissolved sodium carbonate, there is a double displacement reaction resulting in the release of carbon dioxide gas. This effervescence causes the foam to lather even more. The time for this release is about 5 seconds. As the rubbing continues, the second layer of polyvinyl alcohol dissolves thereby releasing the dye. It immediately turns the foam blue. The time required for this action is about 30 seconds.

These numerous examples along with some of the various permutations and combinations of the multiple zone encapsulation system set out in Table 1 used to generate handwashing compositions is not intended to limit the invention to only those permutations and combinations of the multiple zone encapsulation system describe or only to those methods of use described, or solely to handwashing applications, but is intended to be illustrative of the wide variety of single and multiple zone capsules that can be made and the wide variety of applications in which the invention can be used, such as formulations that comprise, individually or in combination, elements, substances, compositions, components, or materials, that are suitable for application to the human skin, hair, or nails such as soaps, shampoos, conditioners, moisturizers, masks, depilatories, lotions, creams, toothpastes, teeth whiteners, make up removers, cuticle oil; or can be useful with respect to: cleaning formulations; pharmaceutical formulations; surface preparation or finishing formulations such as automotive finish cleaners and waxes; upholstery cleaners; carpet cleaners; or the like.

Importantly, it should be understood that the multiple zone encapsulation system can further include a third capsule wall defining a third zone containing a third amount of material, a fourth capsule wall defining a fourth zone, and so forth, each of which can respond to a third activation element or a fourth activation element, if desired.

Also, it should be understood that the materials contained within the zones can further include materials that individually or in combination with the materials of other zone can generate perceivable tactile indicia, auditory indicia, additional visual indicia, or additional fragrance indicia in response to the activation elements selected.

The basic concepts of the invention may be embodied and claimed in a variety of ways. The invention involves a material encapsulation and delivery system; capsules providing one or more zones containing materials; carriers in which such capsules can be conveyed and into which such materials can be released; cosmetics, hand wash agents, and other useful compositions conveying such capsules; and methods of making and using embodiments of the invention.

While specific illustrative examples of the invention are disclosed in the description and drawings, it should be understood that these illustrative examples are not intended to be limiting with respect to the generic nature of the invention which encompasses numerous and varied embodiments; many alternatives are implicit or inherent. Each feature or element of the invention is to be understood to be representative of a broader function or of a great variety of alternative or equivalent elements. Where the feature or element is described in device-oriented terminology, each element of the device is to be understood to perform a function. Neither the description nor the terminology is intended to limit the scope of the claims herein included solely to an apparatus or to a method.

Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "capsule" should be understood to encompass disclosure of the act of "encapsulating"—whether explicitly discussed or not—and, conversely, were there effectively disclosure of the act of "encapsulating", such a disclosure should be understood to encompass disclosure of a "capsule" and even a "means for encapsulating". Such changes and alternative terms are to be understood to be explicitly included in the description.

As such, it should be understood that a variety of changes may be made to the invention as described without departing from the essence of the invention. The disclosure encompassing both the explicit embodiment(s) shown, the great variety of implicit alternative embodiments, and the methods or processes are relied upon to support the claims of this application.

Any patents, publications, or other references mentioned in this application for patent are hereby incorporated by reference. In addition, as to each term used it should be understood that unless its utilization is inconsistent with such interpretation, common dictionary definitions should be understood as incorporated by reference for each term and all definitions, alternative terms, and synonyms such as contained in the Random House Webster's Unabridged Dictionary, second edition.

Thus, the applicant(s) should be understood to claim at least: i) each of the material encapsulation systems as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the related methods disclosed and described, xi) similar, equivalent, and even implicit variations of each of these systems and methods, xii) those alternative designs which accomplish each of the functions shown as are disclosed and described, xiii) those alternative devices and methods which accomplish each of the functions shown as are implicit to accomplish that which is disclosed and described, ivx) each feature, component, and step shown as separate and independent inventions, xv) the various combinations and permutations of each of the above, and xvi) each potentially dependent claim or concept as a dependency on each and every one of the independent claims or concepts presented.

It should be understood for practical reasons, the applicant may initially present only apparatus or method claims and then only with initial dependencies. The applicant does not waive any right to present additional independent or dependent claims which are supported by the description during the prosecution of this application. The applicant specifically reserves all rights to file continuation, division, continuation-in-part, or other continuing applications to claim the various inventions described without limitation by any claim made in a prior application to the generic nature of the invention or the breadth of any claim made in a subsequent application.

Further, the use of the transitional phrase "comprising" is used to maintain "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible.

The claims set forth in this specification are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

We claim:

1. A material release system, comprising:
   a. a first amount of material, wherein said first amount of material comprises a base;
   b. a capsule having a first capsule wall which bounds said first amount of material, wherein said capsule releases said first amount of material in response to a first activation element;
   c. a liquid carrier having a pH of between about 5 and about 7 in which a plurality of said capsules are mixed, and wherein said plurality of capsules do not degrade in said liquid carrier; and
   d. an amount of indicator material mixed into said liquid carrier, wherein release of said first amount of material in response to said first activation element increases said pH of said liquid carrier to greater than 7, and wherein said amount of indicator material dissolved into said liquid carrier changes color in response to increase in said pH.

2. A material release system as described in claim 1, wherein said base is selected from the group consisting of: sodium acetate, sodium carbonate, sodium bicarbonate, sodium borate, sodium citrate, sodium folate, sodium hydroxide, sodium phosphate dibasic, sodium phosphate tribasic, sodium polymetaphosphate, sodium pyrophosphate, sodium glycerophosphate, sodium ortho silicate, sodium meta silicate, sodium hypochlorite, sodium metaborate, sodium perborate, sodium tartrate, trisodium phosphate, potassium salts thereof, and lithium salts thereof.

3. A material release system as described in claim 1, wherein said base comprises a base particle.

4. A material release system as described in claim 1, wherein said base comprises a trisodium phosphate.

5. A material release system as described in claim 4, wherein said trisodium phosphate comprises an anhydrous trisodium phosphate.

6. A material release system as described in claim 4, wherein said trisodium phosphate comprises a trisodium phosphate hydrated with five (5) moles of water.

7. A material release system as described in claim 4, wherein said trisodium phosphate comprises a trisodium phosphate hydrated with nine (9) moles of water.

8. A material release system as described in claim 4, wherein said trisodium phosphate comprises a trisodium phosphate hydrated with twelve (12) moles of water.

9. A material release system as described in claim 4, wherein said trisodium phosphate comprises a trisodium phosphate particle of between about 40 micron and about 250 micron.

10. A material release system as described in claim 4, wherein said trisodium phosphate comprises a trisodium phosphate particle of between about 40 micron and about 100 micron.

11. A material release system as described in claim 4, wherein said trisodium phosphate comprises a trisodium phosphate particle of between about 50 micron and about 80 micron.

12. A material release system as described in claim 4, wherein said trisodium phosphate comprises a plurality of trisodium phosphate particles sieved through a first United States standard mesh 200 and sieved through a second United States standard mesh 270 to provide said plurality of trisodium phosphate particles in the range of between United States standard mesh 200 and United States standard mesh 270.

13. A material release system as described in claim 1, wherein said carrier is selected from the group consisting of: ethylene glycol, propylene glycol, polyethylene glycol, polypropylene glycol, poly(ethylene glycol/propylene glycol), 1,3-propanediol, 1,2-butanediol, 2,3-butanediol, 1,4-butanediol, 1,6-hexanediol, pinacol, glycerol, neopentylglycol, pentaerythritol, meso-hydrobenzoin, 1,2-cyclopentanediol, 1,2-cyclohexanediol, methanol, ethanol, isopropanol, n-propanol, n-butanol, isobutanol, sec-butanol, tert-butanol, n-pentanol, isopentanol, amyl alcohol, tert-pentanol, cyclopentanol, cyclohexanol, n-hexanol, n-heptanol, n-octanol, n-nonanol. n-decanol, n-dodecanol n-tetradecanol, n-hexadecanol, n-octadecanol, phenoxyethanol, benzyl alcohol, diphenyl carbinol, tetraphenylcarbinol, methoxyethanol, ethoxyethanol, propoxyethanol, butoxyethanol, hexoxyethanol, methoxypropanol, ethoxypropanol, propoxypropanol, butoxyepropanol, hexoxypropanol, ethoxyethoxy methanol, ethoxyethoxy ethanol, ethoxyethoxy propanol, ethoxyethoxy butanol, ethoxyethoxy hexanol, propoxypropoxy methanol, propoxypropoxy ethanol, propoxypropoxy propanol, propoxypropoxy butanol, propoxypropoxy hexanol.

14. A material release system as described in claim 13, wherein said amount of indicator material comprises a color change material.

15. A material release system as described in claim 14, wherein said amount of indicator material changes color in response to altered pH of said carrier.

16. A material release system as described in claim 15, wherein said amount of indicator material changes color in response to an increase in pH of said carrier.

17. A material release system as described in claim 16, wherein said amount of indicator is selected from the group consisting of: brilliant yellow, bromothylmol blue, m-nitrophenol, neutral red, phenolphthalein.

18. A material release system as described in claim 17, wherein said carrier has a final pH of between about 7.0 and about 9.4.

19. A material release system as described in claim 18, wherein said carrier comprises a composition suitable as a hand wash agent wherein said capsule releases substantially all of said base not before elapse of about 10 seconds and not after elapse of about 30 seconds.

* * * * *